(12) United States Patent
Kurn et al.

(10) Patent No.: US 8,143,001 B2
(45) Date of Patent: *Mar. 27, 2012

(54) METHODS FOR ANALYSIS OF NUCLEIC ACID METHYLATION STATUS AND METHODS FOR FRAGMENTATION, LABELING AND IMMOBILIZATION OF NUCLEIC ACIDS

(75) Inventors: Nurith Kurn, Palo Alto, CA (US); Geoffrey A. Dafforn, Los Altos, CA (US)

(73) Assignee: NuGEN Technologies, Inc., San Carlos, CA (US)

( * ) Notice: Subject to any disclaimer, the term of this patent is extended or adjusted under 35 U.S.C. 154(b) by 825 days.

This patent is subject to a terminal disclaimer.

(21) Appl. No.: 11/948,784

(22) Filed: Nov. 30, 2007

(65) Prior Publication Data

US 2009/0233804 A1 Sep. 17, 2009

Related U.S. Application Data

(62) Division of application No. 11/026,280, filed on Dec. 29, 2004, now abandoned.

(60) Provisional application No. 60/533,381, filed on Dec. 29, 2003.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ........ 435/6.1; 435/6.2; 435/91.1; 536/23.1; 536/24.3; 536/24.33

(58) Field of Classification Search .............. 435/6, 91.1, 435/183, 6.1, 6.2; 436/94, 501; 536/23.1, 536/24.3, 24.33, 25.3
See application file for complete search history.

(56) References Cited

U.S. PATENT DOCUMENTS

| | | | |
|---|---|---|---|
| 4,362,867 A | 12/1982 | Paddock |
| 4,876,187 A | 10/1989 | Duck et al. |
| 4,996,143 A | 2/1991 | Heller et al. |
| 5,011,769 A | 4/1991 | Duck et al. |
| 5,035,996 A | 7/1991 | Hartley |
| 5,043,272 A | 8/1991 | Hartley |
| 5,082,830 A | 1/1992 | Brakel et al. |
| 5,090,591 A | 2/1992 | Long |
| 5,130,238 A | 7/1992 | Malek et al. |
| 5,169,766 A | 12/1992 | Schuster et al. |
| 5,194,370 A | 3/1993 | Berninger et al. |
| 5,399,491 A | 3/1995 | Kucian et al. |
| 5,409,818 A | 4/1995 | Davey et al. |
| 5,418,149 A | 5/1995 | Gelfand et al. |
| 5,427,929 A | 6/1995 | Richards et al. |
| 5,480,784 A | 1/1996 | Kacian et al. |
| 5,510,270 A | 4/1996 | Fodor et al. |
| 5,545,522 A | 8/1996 | Van Gelder et al. |
| 5,554,516 A | 9/1996 | Kacian et al. |
| 5,554,517 A | 9/1996 | Davey et al. |
| 5,556,752 A | 9/1996 | Lockhart et al. |
| 5,573,913 A | 11/1996 | Rosemeyer et al. |
| 5,578,832 A | 11/1996 | Trulson et al. |
| 5,589,339 A | 12/1996 | Hampson et al. |
| 5,665,549 A | 9/1997 | Pinkel et al. |
| 5,667,976 A | 9/1997 | Van Ness et al. |
| 5,667,979 A | 9/1997 | Berrens |
| 5,679,512 A | 10/1997 | Laney et al. |
| 5,683,879 A | 11/1997 | Laney et al. |
| 5,688,648 A | 11/1997 | Mathies et al. |
| 5,708,154 A | 1/1998 | Smith et al. |
| 5,716,785 A | 2/1998 | Van Gelder et al. |
| 5,726,329 A | 3/1998 | Jones et al. |
| 5,824,517 A | 10/1998 | Cleuziat et al. |
| 5,824,518 A | 10/1998 | Kacian et al. |
| 5,837,832 A | 11/1998 | Chee et al. |
| 5,876,976 A | 3/1999 | Richards et al. |
| 5,888,779 A | 3/1999 | Kacian et al. |
| 5,945,313 A | 8/1999 | Hartley et al. |
| 5,952,176 A | 9/1999 | McCarthy et al. |
| 5,958,681 A | 9/1999 | Wetmur et al. |
| 5,965,409 A | 10/1999 | Pardee et al. |
| 5,972,618 A | 10/1999 | Bloch |
| 6,030,774 A | 2/2000 | Laney et al. |
| 6,037,152 A | 3/2000 | Richards et al. |
| 6,077,674 A | 6/2000 | Schleifer et al. |
| 6,087,103 A | 7/2000 | Burmer |
| 6,090,553 A | 7/2000 | Matson |
| 6,090,591 A | 7/2000 | Berg et al. |

(Continued)

FOREIGN PATENT DOCUMENTS

EP 0365627 B1 5/1990

(Continued)

OTHER PUBLICATIONS

Adamczyk, et al. Synthesis of a Chemiluminescent Acridinium Hydroxylamine (AHA) for the Direct Detection of Abasic Sites in DNA. Org. Lett. 1999; 1(5):779-781.

(Continued)

*Primary Examiner* — Frank W Lu
(74) *Attorney, Agent, or Firm* — Wilson Sonsini Goodrich & Rosati

(57) ABSTRACT

The invention relates to methods for analysis of nucleic acid methylation status, and fragmentation and/or labeling and/or immobilization of nucleic acids. More particularly, the invention relates to methods for fragmentation and/or labeling and/or immobilization of nucleic acids comprising labeling and/or cleavage and/or immobilization at abasic sites.

22 Claims, 1 Drawing Sheet

U.S. PATENT DOCUMENTS

| | | | |
|---|---|---|---|
| 6,159,685 A | 12/2000 | Pinkel et al. | |
| 6,160,105 A | 12/2000 | Cunningham et al. | |
| 6,169,194 B1 | 1/2001 | Thompson et al. | |
| 6,172,208 B1 | 1/2001 | Cook | |
| 6,174,680 B1 | 1/2001 | Makrigiorgos | |
| 6,190,865 B1 | 2/2001 | Jendrisak et al. | |
| 6,194,211 B1 * | 2/2001 | Richards et al. | 435/456 |
| 6,225,451 B1 * | 5/2001 | Ballinger et al. | 536/22.1 |
| 6,251,639 B1 | 6/2001 | Kurn | |
| 6,270,961 B1 | 8/2001 | Drmanac | |
| 6,280,935 B1 | 8/2001 | Macevicz | |
| 6,291,170 B1 | 9/2001 | Van Gelder et al. | |
| 6,306,365 B1 | 10/2001 | Ruoslahti et al. | |
| 6,309,843 B1 | 10/2001 | Timms | |
| 6,326,142 B1 | 12/2001 | Royer et al. | |
| 6,335,167 B1 | 1/2002 | Pinkel et al. | |
| 6,339,147 B1 | 1/2002 | Luktanov et al. | |
| 6,440,705 B1 | 8/2002 | Stanton, Jr. et al. | |
| 6,686,156 B2 | 2/2004 | Kurn | |
| 6,692,918 B2 | 2/2004 | Kurn | |
| 6,815,164 B2 | 11/2004 | Kurn | |
| 6,825,011 B1 | 11/2004 | Romantchikov | |
| 6,858,413 B2 | 2/2005 | Kurn | |
| 6,946,251 B2 | 9/2005 | Kurn | |
| 7,060,441 B2 | 6/2006 | Bourget et al. | |
| 7,094,536 B2 | 8/2006 | Kurn | |
| 7,176,025 B2 | 2/2007 | Kurn et al. | |
| 7,273,730 B2 | 9/2007 | Du Breuil Lastrucci | |
| 7,402,386 B2 | 7/2008 | Kurn et al. | |
| 2001/0000077 A1 | 3/2001 | Engelhardt et al. | |
| 2001/0031739 A1 | 10/2001 | Dare | |
| 2001/0034048 A1 | 10/2001 | Kurn | |
| 2001/0041334 A1 | 11/2001 | Rashtchian et al. | |
| 2002/0028447 A1 | 3/2002 | Li et al. | |
| 2002/0115088 A1 | 8/2002 | Kurn | |
| 2002/0155451 A1 | 10/2002 | Makrigiorgos | |
| 2002/0164628 A1 | 11/2002 | Kurn | |
| 2002/0197639 A1 | 12/2002 | Shia et al. | |
| 2003/0087251 A1 | 5/2003 | Kurn | |
| 2003/0143555 A1 | 7/2003 | Bourget et al. | |
| 2003/0186234 A1 | 10/2003 | Kurn | |
| 2003/0215926 A1 | 11/2003 | Kurn et al. | |
| 2004/0002371 A1 | 1/2004 | Paquin et al. | |
| 2004/0005614 A1 * | 1/2004 | Kurn et al. | 435/6 |
| 2004/0023271 A1 | 2/2004 | Kurn et al. | |
| 2004/0203019 A1 | 10/2004 | Kurn | |
| 2004/0203025 A1 | 10/2004 | Kurn | |
| 2005/0003441 A1 | 1/2005 | Kurn | |
| 2005/0014192 A1 | 1/2005 | Kurn | |
| 2005/0019793 A1 | 1/2005 | Kurn et al. | |
| 2005/0064456 A1 | 3/2005 | Kurn | |
| 2005/0123956 A1 | 6/2005 | Blume et al. | |
| 2005/0136417 A1 | 6/2005 | Cole et al. | |
| 2005/0191682 A1 | 9/2005 | Barone et al. | |
| 2006/0014182 A1 | 1/2006 | Kurn | |
| 2006/0240451 A1 | 10/2006 | Jendrisak et al. | |
| 2008/0176311 A1 | 7/2008 | Kurn | |
| 2008/0182300 A1 | 7/2008 | Kurn | |
| 2009/0068709 A1 | 3/2009 | Kurn et al. | |
| 2009/0130721 A1 | 5/2009 | Kurn et al. | |
| 2009/0203085 A1 | 8/2009 | Kurn et al. | |
| 2009/0203531 A1 | 8/2009 | Kurn et al. | |
| 2009/0239232 A1 | 9/2009 | Kurn et al. | |
| 2009/0275486 A1 | 11/2009 | Kurn et al. | |
| 2010/0022403 A1 | 1/2010 | Kurn et al. | |

FOREIGN PATENT DOCUMENTS

| | | |
|---|---|---|
| EP | 0329822 B1 | 6/1994 |
| EP | 0667393 A2 | 8/1995 |
| EP | 0667393 A3 | 11/1995 |
| EP | 0843735 | 5/1998 |
| EP | 1071811 | 1/2001 |
| WO | WO 92/07951 A1 | 5/1992 |
| WO | WO 93/18052 A1 | 9/1993 |
| WO | WO 97/12061 A1 | 4/1997 |
| WO | WO 97/25416 A2 | 7/1997 |
| WO | WO 97/25416 A3 | 10/1997 |
| WO | WO 98/06736 A1 | 2/1998 |
| WO | WO 98/38296 A1 | 9/1998 |
| WO | WO 99/10540 A1 | 3/1999 |
| WO | WO 99/11819 A1 | 3/1999 |
| WO | WO 99/42618 A1 | 8/1999 |
| WO | WO 00/08208 A2 | 2/2000 |
| WO | WO 00/08208 A3 | 5/2000 |
| WO | WO 00/39345 A1 | 7/2000 |
| WO | WO 00/52191 A1 | 9/2000 |
| WO | WO 01/20035 A2 | 3/2001 |
| WO | WO 01/23613 A1 | 4/2001 |
| WO | WO 01/46464 A1 | 6/2001 |
| WO | WO 01/64952 A2 | 9/2001 |
| WO | WO 01/20035 A3 | 12/2001 |
| WO | WO 02/00938 A2 | 1/2002 |
| WO | WO 02/28876 A2 | 4/2002 |
| WO | WO 02/29117 A2 | 4/2002 |
| WO | WO 02/36821 A2 | 5/2002 |
| WO | WO 02/48402 A2 | 6/2002 |
| WO | WO 02/28876 A3 | 8/2002 |
| WO | WO 02/060318 A2 | 8/2002 |
| WO | WO 02/072772 A2 | 9/2002 |
| WO | WO 02/072773 A2 | 9/2002 |
| WO | WO 02/081753 A1 | 10/2002 |
| WO | WO 02/090584 A2 | 11/2002 |
| WO | WO 01/64952 A3 | 12/2002 |
| WO | WO 02/36821 A3 | 3/2003 |
| WO | WO 03/027259 A2 | 4/2003 |
| WO | WO 02/00938 A3 | 8/2003 |
| WO | WO 02/29117 A3 | 8/2003 |
| WO | WO 02/072772 A3 | 9/2003 |
| WO | WO 02/090584 A3 | 9/2003 |
| WO | WO 03/078645 A2 | 9/2003 |
| WO | WO 02/060318 A3 | 10/2003 |
| WO | WO 03/083435 A2 | 10/2003 |
| WO | WO 02/072773 A3 | 12/2003 |
| WO | WO 03/027259 A3 | 12/2003 |
| WO | WO 03/083435 A3 | 2/2004 |
| WO | WO 03/078645 A3 | 3/2004 |
| WO | WO 02/48402 A3 | 4/2004 |
| WO | WO 2004/011665 A2 | 9/2004 |
| WO | WO 2004/011665 A3 | 7/2005 |
| WO | WO 2005/065321 A2 | 7/2005 |
| WO | WO 2007/030759 A2 | 3/2007 |
| WO | WO 2007/030759 A3 | 6/2007 |
| WO | WO 2007/136717 A1 | 11/2007 |
| WO | WO 2008/005459 A2 | 1/2008 |
| WO | WO 2008/005459 A3 | 2/2008 |
| WO | WO 2005/065321 A3 | 5/2009 |

OTHER PUBLICATIONS

Adamczyk, et al. O-(Fluorosceinylmethyl) hydroxylamine (OFMHA): A Fluorescent Regent for Detection of Damaged Nucleic Acids. Bioorg. & Med. Chem. Lett. 1998; 8:3599-3602.
Ausubel, et al., Eds. Current Protocols in Molecular Biology. John Wiley & Sons, Inc. 1987 and updates.
Ballestar, et al. Methyl-CpG-binding proteins. Targeting specific gene repression. Eur J Biochem 2001; 268:1-6, (contents only).
Bangs Laboratories, Inc. TechNote 205 retreived at: http:bangslab.com/technotes/205.pdf . Visited on Jul. 16, 2003. (8 pages).
Boturyn, et al. A simple and Sensitive Method for in Vitro Quantitation of Abasic Sites in DNA. Chem. Res. Toxicol. 1999; 12:476-482.
Boturyn, et al. Synthesis of Fluorescent Probes for the Detection of Abasic Sites in DNA. Tetrahedron. 1997; 53(15):5485-5492.
Carey, et al. Human Apurinic/Apyrimidinic Endonuclease in Processive. Biochem. 1999; 38:16553-16560.
Derisi, et al. Use of cDNA microarray to analyse gene expression patterns in human cancer. Nature Genetics. 1996; 14:457-460.
Erlanger, et al. Antibodies Specific for Ribonucleosides and Ribonucleotides and Their Reaction With DNA. Proc Natl Acad Sci USA. 1964; 52:68-74.
Fodor, et al. Light-Directed, spatially addressable parallel chemical synthesis. 1991; 251: 767-773.
Freshney, ed. Animal Cell Culture. IRL Press: Oxford, 1987; pp. vii-xii (Table of Contents Only.).
Gait, ed. Oligonucleotide Synthesis: A Practical Approach. IRL Press: Oxford, 1984; pp. vii-xii (Table of Contents).

Ghosh. Synthesis of 5'-Oligonucleotide Hydrazide Derivatives and Their Use in Preparation of Enzyme-Nucleic Acid Hybridization Probes. Anal. Biochem. 1989; 178:43-51.

Hollis, et al. Structural studies of human alkyladenine glycosylase and *E. coli* 3-methyladenine glycosylase.Mutat Res. 2000; 460(3-4):201-10.

Horn, et al. Solid supported hydrolysis of apurinic sites in synthetic oligonucleotides for rapid and efficient purification on reverse-phase cartridges. Nucl. Acids Res. 1988; 16:11559-11571.

Ide, et al. Synthesis and Damage Specificity of a Novel Probe for the Detection of Abasic Sites in DNA. Biochem. 1993; 32:8276-8283.

International Priminary Ecamination Report mailed on Mar. 22, 2006 for PCT Patent Application No. PCT/US03/15825 filed May 19,2003, 9pages.

Kawarada, et al. Antibodies Specific for Methylated DNA Elicited in Rabbits Recognize only a Single Strand Region of DNA Containing 7-Methylguanine. Tohuku. J Exp Med. 1986; 149:151-161.

Khrapko, et al. A method for DNA sequencing by hybridization with oligonucleotide matrix. DNA Sequence- J. DNA Sequencing and Mapping. 1991; 1:375-388.

Kow. Detection of Abasic Sites and Oxidative DNA Base Damage Using an ELISA-like Assay. Methods. 2000; 22:164-169.

Kubo, et al. A Novel Sensitive, and Specific Assay for Abasic Sites, the Most Commonly Produced DNA Lesion. Biochem. 1992; 31:3703-3708.

Lhoome, et al. Abasic DNA Structure reactivity and recognition. Biopolymers. 1999; 52(2): 65-83.

Lindahl. An N-Glycosidase from *Escherichia coli* That Releases Free Uracil from DNA Containing Deaminated Cytosine Residues. Proc Natl. Acad. Sci. USA 1974; 71(9):3649-3653.

Lockhart, et al. Expression monitoring by hybridization to high-density oligonucleotide arrays. Nature Biotechnology. 1996; 14:1675-1680.

Makrigiorgos, et al. Fluorescent labelling of abasic sites: a novel methodology to detect closely-spaced damage sites in DNA. Int J Radiat Biol. 1998; 74(1):99-109.

Maskos, et al. Oligonucleotide hybridisations on glass supports: a novel linker for oligonucleotide synthesis and hybridization properties of oligonucleotides synthesised in Situ. Nucl. Acids. Res. 20(7):1679-1684. 1992.

Maulik, et al. Novel Non-isotopic Detection of MutY Enzyme-recognized Mismatches in DNA Via Ultrasensitive Detection of Aldehydes. Nucl. Acids. Res. 1999: 27(5):1316-1322.

McCarthy, et al. Inducible repair of O-alkylated DNA pyrimidines in *Escherichia coli*. EMBO J. 1984; 3(3):545-50.

McHugh, et al. Novel Regents for Chemical Cleavage at Abasic Sites and UV Photoproducts in DNA. Nucl. Acids. Res. 23(10): 1664-1670, 1995.

Mizugaki, et al. Preparation of a monoclonal antibody specific for 5-methyl-2'-deoxycytidine and its application for the detection of DNA methylation levels in human peripheral blood cells. Biol Pharm Bull. 1996; 19(12):1537-1540.

Molecular Probe Handbook Section 3.2 obtained from website at: http://probes.com/handbook/print/0302.html (Copyright © 1996-2003 by Molecular Probes, Inc.) Visited on Aug. 13, 2003, 16 pages.

Mullis, et al., Eds. *PCR: Polymerase Chain Reaction*. Birkhauser: Boston, 1994; pp. xv-xvii (Table of Contents).

Nakamura. Highly Sensitive Apurinic/Apyrimidinic site Assay Can Detect Spontaneous and Chemically Induced Depurination Under Physiological Conditions. Cancer Res. 1998; 58:222-225.

Nedderman, et al. Cloning and expression of human G/T mismatch-specific thymine-DNA glycosylase. J Biol Chem. 1996; 271(22):12767-74.

O'Shannessy Immobilization of Glycoconjugates by Their Oligosaccharides: Use of Hydrazido-Derivatized Matrices. Anal. Biochem. 1990; 191:1-8.

Pang, et al. Use of modified nucleotides and uracil-DNA glycosylase (UNG) for the control of contamination in the PCR-based amplification of RNA. Molecular and Cellular Probes. 1992; 6:251-256.

Pease, et al. Light-generated oligonucleotide arrays for rapid DNA sequence analysis. Proc. Natl. Acad. Sci. USA 1994; 91:5022-5026.

Proudnikov, et al. Chemical methods of DNA and RNA fluorescent labeling. Nucleic Acids Res. Nov. 15, 1996;24(22):4535-42.

Sambrook, et al., Eds. Molecular Cloning: A Laboratory Manual. 2nd Edition, Cold Spring Harbor Laboratory Press, 1989; pp. xi-xxxviii (Table of Contents).

Sano, et al. Detection of heavy methylation in human repetitive DNA subsets by a monoclonal antibody against 5-methylcytosine. Biochim Biophys Acta. 1988; 951(1):157-65.

Sartori, et al. A novel uracil-DNA glycosylase with broad substrate specificity and an unusual active site. EMBO J. 2002; 21(12):3182-91.

Schena, et al. Parallel human genome analysis: microarray-based espression monitoring of 1000 genes. Proc Natl. Acad. Sci. USA Biochemistry. 1996; 93:10614-10619.

Schena, et al. Quantitative monitoring of gene expression patterns with a complementary DNA microarray. Science. 1995; 270:467-470.

Shalon, et al. A DNA microarray system for analyzing complex DNA samples using two-color fluorescent probe hybridization. Genome Res. 1996; 6:639-645.

Shida, et al. Cleavage of Single-and double-Stranded DNAs Containing an Abasic Residue by *Escherichia coli* Exonuclease III (AP Endonuclease VI) Nucl. Acids. Res. 1996; 24(22):4572-4576.

Sluppheug, et al. Low incorporation of dUMP by some thermostable DNA polymerases may limit their use in PCR amplifications. Anal. Biochem. 1993; 211:164-169.

Sohail, et al. Human activation-induced cytidine deaminase causes transcription-dependent, strand-biased C to U deaminations. Nucleic Acids Res. 2003; 31(12):2990-4.

Srivastava, et al. Mammalian Abasic Site Base Excision Repair. Identification of the Reaction Sequence and Rate-Determining Steps. J. Biol. Chem. 1998; 273(33):21203-21209.

Steullet, et al. Cleavage of Abasic Sites in DNA by Intercalator-amines. Bioorgan. Med Chem. 1991; 7:2531-2540.

Stratagene catalog, Gene Characterizatin Kits. 1988 p. 39.

Sugiyama, et al. Chemistry of thermal degradation of abasic sites in DNA. Mechanistic investigation on thermal DNA stand clevage of alkylated DNA. Chem. Res. Toxicol. 1994; 7:673-683.

Vairapandi, et al. Partial purification and characterization of human 5-methylcytosine-DNA glycosylase. Oncogene. 1996; 13(5):933-8.

Vairapandi, et al. Human DNA-demethylating activity: a glycosylase associated with RNA and PCNA. J Cell Biochem. 2000; 79(2):249-60.

Wilchek, et al. Labeling Glycoconjugates with Hydrazide Reagents. Methods Enzymol. 1987; 138:429-442.

Wolffe, et al. DNA demethylation. Proc Natl Acad Sci USA. 1999; 96(11):5894-6.

Yoke, et al. Detection of abasic sites and oxidatie DNA base damage using an ELISA-like assay. Methods. 2000, vol. 22: 164-169.

Zalipsky. Functionalized Poly(ethylene glycol) for Preparation of Biologically Relevant Congugates. Bioconjugate Chem. 1995; 6:150-165.

Zhu, et al. Overexpression of 5-methylcytosine DNA glycosylase in human embryonic kidney cells EcR293 demethylates the promoter of a hormone-regulated reporter gene. Proc Natl Acad Sci USA. 2001; 98(9):5031-6.

Zhu, et al. 5-Methylcytosine DNA glycosylase activity is also present in the human MBD4 (G/T mismatch glycosylase) and in a related avian sequence. Nucleic Acids Res. 2000; 28(21):4157-65.

Zang, et al. DNA alkylation by leinamycin can be triggered by cyanide and phosphines. Bioorg Med Chem Lett. Jun 18, 2001;11(12):1511-5.

Kim, et al. Evidence for thiol-dependent production of oxygen radicals by 4-methyl-5-pyrazinyl-3H-1,2-dithiole-3-thione (oltipraz) and 3H-1,2-dithiole-3-thione: possible relevance to the anticarcinogenic properties of 1,2-dithiole-3-thiones. Chem Res Toxicol. Mar. 1997;10(3):296-301.

Mitra, et al. Oxidative DNA cleavage by the antitumor antibiotic leinamycin and simple 1,2-dithiolan-3-one 1-oxides: Evidence for thiol-dependent conversion of molecular oxygen to DNA-cleaving oxygen radicals mediated by polysulfides. Journal of the American Chemical Society. 1997; 119(48):11691-11692.

Nugen, Inc. Ovation Biotin RNA Amplification and Labeling System User Guite. Catalog #2300-12. Published 2004.

Nugen, Inc. Technical Report #1. The Ovation Biotin System Validation for Use with Affymetrix GeneChip Arrays. Published 2004.

Ben-Artzi, et al. Double-stranded RNA-dependent RNase activity associated with human immunodeficiency virus type 1 reverse transcriptase. Proc Natl Acad Sci U S A. Feb. 1, 1992;89(3):927-31.

Brown, T.A. Ed. Molecular Biology, LabFax. Bios Scientific Publishers. Academic Press. 1991; pp. 147-148.

European search report dated Oct. 18, 2007 for Application No. 3771533.1.

European search report dated Feb. 12, 2010 for Application No. 7810169.8.

Hottiger, et al. Strand displacement activity of the human immunodeficiency virus type 1 reverse transcriptase heterodimer and its individual subunits. J Biol Chem. Jan. 14, 1994;269(2):986-91.

Huber, et al. Processing of the primer for plus strand DNA synthesis by human immunodeficiency virus 1 reverse transcriptase. J Biol Chem. Jun. 25, 1990;265(18):10565-73.

International search report dated Jan. 2, 2008 for PCT Application No. US2007/15409.

International search report dated Jun. 14, 2005 for PCT Application No. US 2003/015825.

International search report dated Jul. 9, 2008 for PCT Application No. US2004/043710.

European search report dated Mar. 29, 2010 for Application No. 4815722.6.

Buchman, et al. Selective RNA amplification: a novel method using dUMP-containing primers and uracil DNA glycosylase. PCR Methods Appl. Aug. 1993;3(1):28-31.

International search report and written opinion dated Dec. 3, 2010 for PCT Application No. US10-45384.

Karata, et al. Construction of a circular single-stranded DNA template containing a defined lesion. DNA Repair (Amst). Jul. 4, 2009;8(7):852-6.

Heimgartner, et al.Polyacrylic Polyhydrazides as Reagents for Detection of Glycoproteins. Anal. Biochem. 1989; 181:182-189.

Shida, et al. Cleavage of Single:and double-Stranded DNAs Containing an Abasic Residue by *Escherichia coli* Exonuclease III (AP Endonuclease VI) Nucl. Acids. Res. 1996; 24(22):4572-4576.

Burrows, et al. Oxidative Nucleobase Modifications Leading to Strand Scission. Chem Rev. May 7, 1998;98(3):1109-1152.

European office action dated Apr. 1, 2011 for Application No. 03771533.1.

Haraguchi, et al. Synthesis and characterization of oligodeoxynucleotides containing formamidopyrimidine lesions and nonhydrolyzable analogues. J Am Chem Soc. Apr 3, 2002;124(13):3263-9.

\* cited by examiner

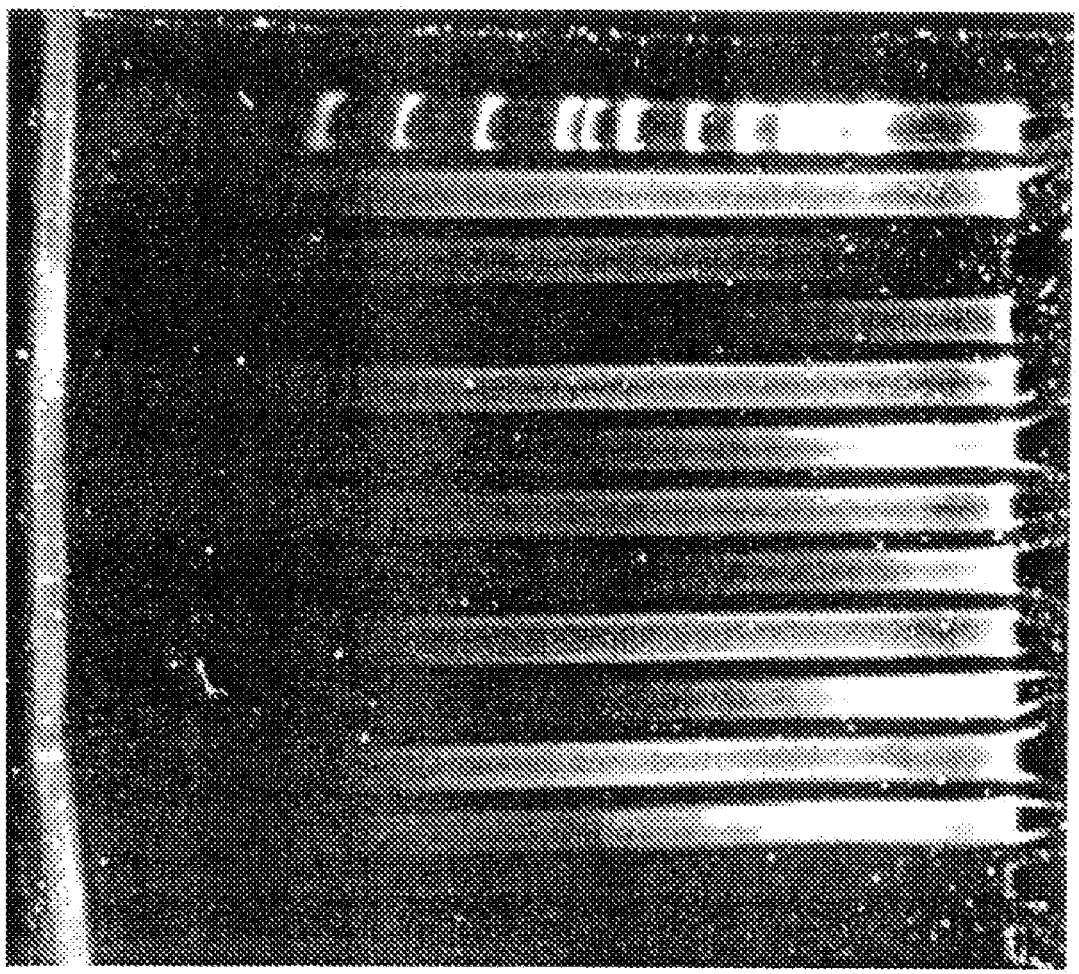

```
SEQUENCE LISTING

<160> NUMBER OF SEQ ID NOS: 1

<210> SEQ ID NO 1
<211> LENGTH: 14
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 1
gacggaugcg gucu                                                      14
```

METHODS FOR ANALYSIS OF NUCLEIC ACID METHYLATION STATUS AND METHODS FOR FRAGMENTATION, LABELING AND IMMOBILIZATION OF NUCLEIC ACIDS

CROSS-REFERENCE TO RELATED APPLICATIONS

This application is a divisional of prior U.S. application Ser. No. 11/026,280, filed on Dec. 29, 2004, now abandoned, which claims the benefit of U.S. Provisional Application No. 60/533,381, filed on Dec. 29, 2003, the disclosure of U.S. Provisional Application No. 60/533,381 is incorporated herein by reference in its entirety.

TECHNICAL FIELD

The invention relates to methods for analysis of nucleic acid methylation status, and methods for fragmentation and/or labeling and/or immobilization of nucleic acids. More particularly, the invention relates to methods for fragmentation and/or labeling and/or immobilization of nucleic acids comprising labeling and/or cleavage and/or immobilization at abasic sites.

BACKGROUND

Methylation of DNA is involved in both normal and abnormal cellular processes. For example, DNA methylation has been implicated in X-inactivation, genomic imprinting, and differential gene expression (such as by upregulation or silencing of genetic loci). DNA methylation plays a role in gene inactivation, cell differentiation, tumorigenesis, X-chromosome inactivation, and is required for mammalian development (Li, et al., Cell 69:915-926, 1992; Okano et al., Cell 99:247-57, 1999). In bacteria, methylation of cytosine and adenine residues plays a role in the regulation of DNA replication and DNA repair. DNA methylation has also been associated with increased risk of cancer, as well as cancer development itself.

Methylation of DNA is carried out by methylases (also known as methyltransferases). These enzymes are generally sequence-specific, and they can methylate both nucleic acid strands (in the case of DNA). Replication of these strands yields a hemi-methylated state which is recognized by a class of maintenance methylases capable of restoring full methylation to both strands.

Methylation can occur at all nucleotide residues, although in mammalian species, DNA methylation commonly occurs at cytosine residues, and more commonly at cytosine residues that lie next to a guanosine residue, i.e., at cytosine residues of a CG dinucleotide. CG dinucleotides in "CpG islands" remain methylation-free. CpG islands are rich in CG sites and are often found near coding regions within the genome (i.e., genes). About half of the genes in the human genome are associated with CpG islands. Importantly, the vast majority of CpG islands in the genome remain unmethylated in normal adult cells and tissues. Methylation of CpG islands is normally seen only on the inactive X-chromosome in females and at imprinted genes where it functions in the stable silencing of such genes. Strict control over the levels and distribution of DNA methylation are essential to normal animal development.

Alteration in DNA methylation is one manifestation of the genome instability characteristic of human tumors. A hallmark of human carcinogenesis is the loss of normal constraints on cell growth resulting from genetic alterations in the genes that control cell growth. The consequences of such mutations include the activation of positive growth signals and the inactivation of growth inhibitory signals. Identification of gene targets which when methylated lead to the loss of normal cell responses would be valuable. This would facilitate the diagnosis and treatment of disorders associated with abnormal methylation and any downstream events resulting therefrom.

The level of methylation of a nucleic acid can be determined using a number of techniques available in the art. Some methods of analysis involve the use of the chemical regent, bisulfite. Other methods for methylation analysis include methylation-sensitive restriction analysis, methylation-specific polymerase chain reaction (MSP), sequencing of bisulfite-modified DNA, Ms-SnuPE, and COBRA.

There is a serious need for improved methods for analyzing nucleic acid methylation status.

Fragmentation and labeling of nucleic acids are important for the analysis of nucleic acid sequences. For example, fragmentation and/or labeling are commonly required for detection of sequences by binding of a sample nucleic acid to complementary sequences immobilized on a surface, for example, on a microarray. Cleavage of sample nucleic acid into small fragments (e.g., 50-100 base pairs) facilitates diffusion of nucleic acid onto the surface, and may facilitate hybridization. It is known, for example, that steric and charge hindrance effects increase with the size of nucleic acids that are hybridized. Moreover, cleavage of sample nucleic acids into small fragments may ensure that two sequences of interest in the sample do not appear to bind to the same template nucleic acid simply by virtue of their proximity on the test nucleic acid. Cleavage of nucleic acids also facilitates detection of hybridized nucleic acid when, as in many detection methods, the size of the signal is proportional to the size of the bound fragment and thus, control of fragment size is desirable. Labeling of nucleic acids is necessary in many methods of nucleic acid analysis because there are presently few techniques for direct detection of unlabeled nucleic acid with the requisite sensitivity for analysis on chips. Methods for fragmenting and/or labeling nucleic acids are known in the art. See, e.g., U.S. Pat. Nos. 5,082,830; 4,996,143; 5,688,648; 6,326,142; and PCT Publication No. WO 02/090584, and references cited therein.

Immobilization of nucleic acids to create, for example, microarrays or tagged analytes, is useful for, e.g., detection and analysis of nucleic acids and tagged analytes. Methods for immobilizing nucleic acids are known in the art. See, e.g., U.S. Pat. Nos. 5,667,979; 6,077,674; 6,280,935; and references cited therein.

There is a serious need for improved methods for labeling and/or fragmenting and/or immobilizing nucleic acids to a surface (such as a microarray).

All references cited herein, including patent applications and publications, are incorporated by reference in their entirety.

SUMMARY OF THE INVENTION

In one aspect, the invention provides methods for labeling and fragmenting a polynucleotide comprising a methylated nucleotide comprising: (a) contacting a polynucleotide comprising (in some embodiments, suspected of comprising) a methylated nucleotide with an agent capable of cleaving a base portion of the methylated nucleotide (i.e., cleaving a base portion of the methylated nucleotide), whereby an abasic site is generated; (b) cleaving the backbone of the polynucleotide comprising the abasic site at the abasic site; and (c) contacting the polynucleotide comprising the abasic site with an agent capable of labeling the abasic site (i.e., labeling the abasic site), whereby labeled polynucleotide fragments are generated. In some embodiments, the agent capable of cleaving the base portion of the methylated nucleotide is selected from the group consisting of an enzyme, a chemical agent, and acidic conditions. In some embodiments, cleavage of the phosphodiester backbone of a polynucleotide is performed with an agent selected from the group consisting of an enzyme, a chemical agent, acidic conditions, basic conditions, and heat. Two or more of the steps described above may be performed simultaneously, or the steps may be performed sequentially. For example, steps (a), (b), and (c) may be performed simultaneously, steps (a) and (b) may be performed simultaneously, or steps (b) and (c) may be performed simultaneously. When the steps are performed sequentially, step (b) may be performed before step (c) or step (c) may be performed before step (b).

In another aspect, the invention provides methods for labeling a polynucleotide comprising a methylated nucleotide, comprising: (a) cleaving a base portion of the methylated nucleotide with an agent capable of cleaving the base portion of the methylated nucleotide, whereby an abasic site is generated; and (b) labeling at the abasic site, whereby a labeled polynucleotide is generated.

In another aspect, the invention provides a method for fragmenting a polynucleotide comprising a methylated nucleotide, comprising: (a) cleaving a base portion of the methylated nucleotide with an agent capable of cleaving the base portion of the methylated nucleotide whereby an abasic site is generated; and (b) cleaving the backbone of the polynucleotide comprising the abasic site at the abasic site, whereby polynucleotide fragments are generated.

In another aspect, the invention provides methods for fragmenting and labeling a polynucleotide comprising a methylated nucleotide, comprising: (a) incubating a reaction mixture, said reaction mixture comprising: (i) a polynucleotide comprising a methylated nucleotide; and (ii) an agent capable of specifically cleaving a base portion of a methylated nucleotide; wherein the incubation is under conditions that permit cleavage of the base portion of the methylated nucleotide, whereby a polynucleotide comprising an abasic site is generated; (b) incubating a reaction mixture, said reaction mixture comprising: (i) a polynucleotide comprising an abasic site; and (ii) an agent capable of effecting (generally, specific) cleavage of a phosphodiester backbone at the abasic site; wherein the incubation is under conditions that permit cleavage of the phosphodiester backbone at the abasic site; whereby fragments of the polynucleotide are generated; (c) incubating a reaction mixture, said reaction mixture comprising: (i) a polynucleotide comprising an abasic site; and (ii) an agent capable of labeling the abasic site; wherein the incubation is under conditions that permit labeling at the abasic site; whereby labeled fragments are generated.

In one embodiment, the invention provides a method for fragmenting a polynucleotide comprising a methylated nucleotide, said method comprising cleaving the phosphodiester backbone of a polynucleotide comprising an abasic site at the abasic site, wherein the abasic site is generated by cleaving a base portion of a methylated nucleotide with an agent capable of cleaving the base portion of the methylated nucleotide, whereby an abasic site is generated. In another embodiment, the invention provides a method for fragmenting and labeling a polynucleotide comprising a methylated nucleotide, said method comprising cleaving the phosphodiester backbone of a polynucleotide comprising an abasic site at the abasic site, wherein the abasic site is generated by cleaving a base portion of a methylated nucleotide with an agent capable of cleaving the base portion of the methylated nucleotide, and labeling at the abasic site, whereby a labeled polynucleotide fragment is generated. In another embodiment, the invention provides a method for labeling a polynucleotide comprising a methylated nucleotide, said method comprising labeling at the abasic site of a polynucleotide comprising an abasic site, whereby a labeled polynucleotide is generated, wherein the abasic site is generated by cleaving a base portion of a methylated nucleotide with an agent capable of cleaving the base portion of the methylated nucleotide, whereby an abasic site is generated. In another embodiment, the invention provides a method for labeling a polynucleotide fragment, said method comprising labeling at an abasic site of a polynucleotide fragment comprising the abasic site, whereby a labeled polynucleotide fragment is generated, wherein the abasic site is generated by cleaving a base portion of a methylated nucleotide with an agent capable of cleaving the base portion of the methylated nucleotide, and wherein the polynucleotide fragment is generated by cleaving the phosphodiester backbone of the polynucleotide comprising the abasic site at the abasic site.

In one aspect, the invention provides methods for labeling and fragmenting a polynucleotide comprising a methylated nucleotide, said methods comprising: (a) contacting a polynucleotide comprising (in some embodiments, suspected of comprising) a methylated nucleotide with an agent (such as an enzyme) capable of cleaving a base portion of an unmethylated nucleotide (i.e., cleaving a base portion of the unmethylated nucleotide), whereby an abasic site is generated, wherein the agent (such as an enzyme) is not capable of cleaving a methylated nucleotide; (b) cleaving the backbone of the polynucleotide comprising the abasic site at the abasic site; and (c) contacting the polynucleotide comprising the abasic site with an agent capable of labeling the abasic site (i.e., labeling the abasic site), whereby labeled polynucleotide fragments are generated. In some embodiments, the agent capable of cleaving a base portion of an unmethylated nucleotide comprises an enzyme. In one embodiment, the unmethylated nucleotide is cytosine and the enzyme is cytosine deaminase in conjunction with uracil DNA glycosylase. In some embodiments, cleavage of a phosphodiester backbone of a polynucleotide is performed with an agent selected from the group consisting of an enzyme, a chemical agent, acidic conditions, basic conditions, and heat. Two or more of the steps described above may be performed simultaneously, or the steps may be performed sequentially. For example, steps (a), (b), and (c) may be performed simultaneously, steps (a) and (b) may be performed simultaneously, or steps (b) and (c) may be performed simultaneously. When the steps are performed sequentially, step (b) may be performed before step (c) or step (c) may be performed before step (b).

In another aspect, the invention provides a method for producing a labeled polynucleotide comprising a methylated nucleotide, comprising: (a) cleaving a base portion of an unmethylated nucleotide with an agent capable of cleaving the base portion of the unmethylated nucleotide, whereby an abasic site is generated, wherein the agent is not capable of cleaving the base portion of a methylated nucleotide; and (b) labeling at the abasic site, whereby a labeled polynucleotide is generated.

In another aspect, the invention provides a method for fragmenting a polynucleotide comprising a methylated nucleotide, comprising: (a) cleaving a base portion of an unmethylated nucleotide with an agent capable of cleaving the base portion of the unmethylated nucleotide, whereby an abasic site is generated, wherein the agent is not capable of cleaving the base portion of a methylated nucleotide; and (b) cleaving the backbone of the polynucleotide comprising the abasic site, whereby polynucleotide fragments are generated.

In another aspect, the invention provides method for fragmenting and labeling a polynucleotide comprising a methylated nucleotide, comprising: (a) incubating a reaction mixture, said reaction mixture comprising: (i) a polynucleotide comprising a methylated nucleotide; and (ii) an agent capable of cleaving a base portion of a unmethylated nucleotide; wherein the incubation is under conditions that permit cleavage of the base portion of the unmethylated nucleotide, wherein the agent is not capable of cleaving a methylated nucleotide, whereby a polynucleotide comprising an abasic site is generated; (b) incubating a reaction mixture, said reaction mixture comprising: (i) a polynucleotide comprising an abasic site; and (ii) an agent capable of effecting (generally, specific) cleavage of a phosphodiester backbone at the abasic site; wherein the incubation is under conditions that permit cleavage of the phosphodiester backbone at the abasic site; whereby fragments of the polynucleotide are generated; (c) incubating a reaction mixture, said reaction mixture comprising: (i) a polynucleotide comprising an abasic site; and (ii) an agent capable of labeling the abasic site; wherein the incubation is under conditions that permit labeling at the abasic site; whereby labeled fragments are generated.

In one embodiment, the invention provides a method for fragmenting a polynucleotide comprising a methylated nucleotide, said method comprising cleaving the phosphodiester backbone of a polynucleotide comprising an abasic site at the abasic site, wherein the abasic site is generated by cleaving a base portion of an unmethylated nucleotide with an agent capable of cleaving the base portion of the unmethylated nucleotide, whereby an abasic site is generated, wherein the agent is not capable of cleaving a methylated nucleotide. In another embodiment, the invention provides a method for fragmenting and labeling a polynucleotide comprising a methylated nucleotide, said method comprising cleaving the phosphodiester backbone of a polynucleotide comprising an abasic site at the abasic site, wherein the abasic site is generated by cleaving a base portion of an unmethylated nucleotide with an agent capable of cleaving the base portion of the unmethylated nucleotide, whereby an abasic site is generated, wherein the agent is not capable of cleaving a methylated nucleotide, and labeling at the abasic site, whereby a labeled polynucleotide fragment is generated. In another embodiment, the invention provides a method for labeling a polynucleotide comprising a methylated nucleotide, said method comprising labeling at the abasic site of a polynucleotide comprising an abasic site, whereby a labeled polynucleotide is generated, wherein the abasic site is generated by cleaving a base portion of an unmethylated nucleotide with an agent capable of cleaving the base portion of the unmethylated nucleotide, whereby an abasic site is generated, wherein the agent is not capable of cleaving a methylated nucleotide. In another embodiment, the invention provides a method for labeling a polynucleotide fragment, said method comprising labeling at an abasic site of a polynucleotide fragment comprising the abasic site, whereby a labeled polynucleotide fragment is generated, wherein the abasic site is generated by cleaving a base portion of an unmethylated nucleotide with an agent capable of cleaving the base portion of the unmethylated nucleotide, and wherein the polynucleotide fragment is generated by cleaving the phosphodiester backbone of the polynucleotide comprising the abasic site at the abasic site.

In another aspect, the invention provides methods using the labeled and/or fragmented methylated polynucleotides generated using the methods for labeling and/or fragmenting a methylated polynucleotide described herein for, e.g., detection of methylation (including presence and/or absence and/or quantity or level of methylation), identification of methylated polynucleotide sequences, isolation of methylated polynucleotide sequences, characterization of methylated polynucleotide sequences, and other applications as described herein. In one embodiment, the invention provides a method for characterizing a methylated polynucleotide, comprising detecting a polynucleotide fragment or a labeled polynucleotide fragment produced by any of the methods described herein, wherein detection of the polynucleotide fragment correlates with presence, absence, sequence, or amount of the methylated polynucleotide.

In another aspect, the invention provides methods for labeling and fragmenting a polynucleotide comprising a canonical nucleotide, said methods comprising: (a) cleavage of a base portion of a canonical nucleotide present in a polynucleotide comprising the canonical nucleotide with an agent (such as an enzyme) capable of cleaving a base portion of the canonical nucleotide (whereby an abasic site is generated); (b) cleavage of the phosphodiester backbone at the abasic site, and (c) labeling at the abasic site, whereby labeled polynucleotide fragments are generated. In some embodiments, the agent capable of cleaving a base portion of a canonical nucleotide comprises an enzyme. In one embodiment, the canonical nucleotide is cytosine and the enzyme comprises cytosine deaminase in conjunction with uracil DNA glycosylase. In some embodiment, cleavage of the phosphodiester backbone of a polynucleotide is performed with an agent selected from the group consisting of an enzyme, a chemical agent, acidic conditions, basic conditions, and heat. Two or more of the steps described above may be performed simultaneously, Or the steps may be performed sequentially. For example, steps (a), (b), and (c) may be performed simultaneously, steps (a) and (b) may be performed simultaneously, or steps (b) and (c) may be performed simultaneously. When the steps are performed sequentially, step (b) may be performed before step (c) or step (c) may be performed before step (b).

In another aspect, the invention provides methods for fragmenting and labeling a polynucleotide comprising a canonical nucleotide: (a) incubating a reaction mixture, said reaction mixture comprising: (i) a polynucleotide comprising a canonical nucleotide; and (ii) an agent capable of specifically cleaving a base portion of a canonical nucleotide; wherein the incubation is under conditions that permit cleavage of the base portion of the canonical nucleotide, whereby a polynucleotide comprising an abasic site is generated; (b) incubating a reaction mixture, said reaction mixture comprising: (i) a polynucleotide comprising an abasic site; and (ii) an agent capable of effecting (generally, specific) cleavage of a phosphodiester backbone at the abasic site; wherein the incubation is under conditions that permit cleavage of the phosphodiester backbone at the abasic site; whereby fragments of the polynucleotide are generated; (c) incubating a reaction mixture, said reaction mixture comprising: (i) a polynucleotide comprising an abasic site; and (ii) an agent capable of labeling the abasic site; wherein the incubation is under conditions that permit labeling at the abasic site; whereby labeled fragments are generated.

In another aspect, the invention provides methods for labeling a polynucleotide comprising a canonical nucleotide, said methods comprising (a) cleavage of a base portion of a canonical nucleotide present in a polynucleotide comprising the canonical nucleotide with an agent (such as an enzyme)

capable of cleaving a base portion of the canonical nucleotide (whereby an abasic site is generated); and (b) labeling at the site of incorporation of the canonical nucleotide (i.e., at the abasic site), whereby a labeled polynucleotide(s) is generated.

In another aspect, the invention provides methods for fragmenting a polynucleotide comprising a canonical nucleotide, said methods comprising: (a) cleavage of a base portion of a canonical nucleotide present in a polynucleotide comprising the canonical nucleotide with an agent (such as an enzyme) capable of cleaving a base portion of the canonical nucleotide (whereby an abasic site is generated); and (b) cleavage of the phosphodiester backbone at the abasic site, whereby polynucleotide fragments are generated.

In one embodiment, the invention provides a method for fragmenting a polynucleotide comprising a canonical nucleotide, said method comprising cleaving the phosphodiester backbone of a polynucleotide comprising an abasic site at the abasic site, wherein the abasic site is generated by cleaving a base portion of a canonical nucleotide with an agent capable of cleaving the base portion of the canonical nucleotide, whereby an abasic site is generated. In another embodiment, the invention provides a method for fragmenting and labeling a polynucleotide comprising a canonical nucleotide, said method comprising cleaving the phosphodiester backbone of a polynucleotide comprising an abasic site at the abasic site, wherein the abasic site is generated by cleaving a base portion of a canonical nucleotide with an agent capable of cleaving the base portion of the canonical nucleotide, whereby an abasic site is generated, and labeling at the abasic site, whereby a labeled polynucleotide fragment is generated. In another embodiment, the invention provides a method for labeling a polynucleotide comprising a canonical nucleotide, said method comprising labeling at the abasic site of a polynucleotide comprising an abasic site, whereby a labeled polynucleotide is generated, wherein the abasic site is generated by cleaving a base portion of a canonical nucleotide with an agent capable of cleaving the base portion of the canonical nucleotide, whereby an abasic site is generated. In another embodiment, the invention provides a method for labeling a polynucleotide fragment, said method comprising labeling at an abasic site of a polynucleotide fragment comprising the abasic site, whereby a labeled polynucleotide fragment is generated, wherein the abasic site is generated by cleaving a base portion of a canonical nucleotide with an agent capable of cleaving the base portion of a canonical nucleotide, and wherein the polynucleotide fragment is generated by cleaving the phosphodiester backbone of the polynucleotide comprising the abasic site at the abasic site.

In some embodiments, the polynucleotide comprising the canonical nucleotide (that is to be cleaved by the agent that cleaves a base portion of the canonical nucleotide) can be single stranded, double-stranded or partially double stranded. In some embodiments, the polynucleotide comprises a cDNA. In other embodiments, the polynucleotide comprises RNA, mRNA, genomic DNA, or synthetic DNA. In other embodiments, the polynucleotide comprises a cDNA library, a subtractive hybridization library, or a genomic library.

In some embodiments, the invention provides methods wherein the cleavage of the base portion of the cleavable canonical nucleotide is under the same conditions (using the same agent) as the cleavage of the backbone at the abasic site, and labeling at the abasic site. In some embodiments, the reaction conditions are acidic reaction conditions (such as pH 3, pH 3.5 or pH 4). In still other embodiments, labeling and fragmentation (including cleavage of the base portion of the canonical nucleotide and cleavage of the phosphodiester backbone at an abasic site) are under the same conditions (using the same agent). In still other embodiments, the reaction conditions are acidic reaction conditions (such as pH 3, pH 3.5 or pH 4).

The methods of the invention involving cleavage of a cleavable canonical nucleotide include methods using the labeled polynucleotide fragments and labeled polynucleotides produced by the methods of the invention (so-called "applications"). The invention provides methods to characterize (for example, detect presence or absence of and/or quantify) a sequence of interest by analyzing the labeled and/or fragmented products by detection/quantification methods such as those based on array technologies or solution phase technologies. In some embodiments, the invention provides methods of detecting the presence or absence of mutations.

In other embodiments, the invention provides methods of producing a hybridization probe or target, hybridization using the hybridization probes or targets; detection using the hybridization probes or targets; characterizing and/or quantitating nucleic acid, preparing a subtractive hybridization probe, comparative genomic hybridization, and determining a gene expression profile, using the labeled and/or fragmented nucleic acids generated by the methods of the invention. Any of the methods described herein may be used to generated labeled polynucleotides and/or polynucleotide fragments which may be used as hybridization probes or targets. Labeled or unlabeled targets produced by a method of the invention may be hybridized to a probe.

The invention also provides methods for the generation of polynucleotides, or fragments thereof, immobilized to a substrate (surface), e.g., hybridization probes. In some embodiments, the immobilized polynucleotide, or immobilized polynucleotide fragment (in embodiments involving fragmentation) is labeled according to the labeling methods described herein. These methods are suitable for, for example, the production of microarrays or tagged analytes.

As is evident to one skilled in the art, aspects that refer to combining and incubating the resultant mixture also encompasses method embodiments which comprise incubating the various mixtures (in various combinations and/or subcombinations) so that the desired products are formed. The reaction mixtures may be combined (thus reducing the number of incubations) in any way, with one or more reaction mixtures above combined. It is understood that any combination of these incubation steps, and any single incubation step, to the extent that the incubation is performed as part of any of the methods described herein, fall within the scope of the invention.

One or more steps may be combined and/or performed sequentially (often in any order, as long as the requisite product(s) are able to be formed), and, as is evident, the invention includes various combinations of the steps described herein. It is also evident, and is described herein, that the invention encompasses methods in which the initial, or first, step is any of the steps described herein. Methods of the invention encompass embodiments in which later, "downstream" steps are an initial step.

The invention also provides compositions, kits, complexes, reaction mixtures and systems comprising various components (and various combinations of the components) used in the methods described herein. In one aspect, the invention provides a composition comprising an agent capable of cleaving a base portion of a methylated nucleotide to produce an abasic site on a polynucleotide and an agent capable of labeling at an abasic site on a polynucleotide. In one embodiment, the composition further comprises an agent capable of cleaving a phosphodiester backbone of a polynucleotide at an abasic site. In another aspect, the invention provides a composition comprising an agent capable of cleaving a base portion of a canonical nucleotide to produce an abasic site on a polynucleotide and an agent capable of labeling at an abasic site on a polynucleotide. In one embodiment, the composition further comprises an agent capable of cleaving a phosphodiester backbone of a polynucleotide at an abasic site on a polynucleotide. In another aspect, the invention provides a composition comprising a population of labeled and/or fragmented polynucleotides produced by any of the methods described herein. Compositions of the invention may also optionally further comprise a composite primer comprising a DNA portion and a 5' RNA portion.

In another aspect, the invention provides a kit comprising an agent capable of cleaving a base portion of a methylated nucleotide to produce an abasic site on a polynucleotide and an agent capable of labeling at an abasic site on a polynucleotide. In one embodiment, the kit comprises an agent capable of cleaving a phosphodiester backbone of a polynucleotide at an abasic site. In another aspect, the invention provides a kit comprising an agent capable of cleaving a base portion of a canonical nucleotide to produce an abasic site on a polynucleotide and an agent capable of labeling at an abasic site on a polynucleotide. In one embodiment, the kit comprises an agent capable of cleaving a phosphodiester backbone of a polynucleotide at an abasic site. Kits of the invention may also optionally further comprise a composite primer comprising a DNA portion and a 5' RNA portion.

DESCRIPTION OF THE FIGURE

FIG. 1: is a photograph of a gel showing the labeled and fragmented polynucleotide generated by acid-catalyzed cleavage fragmentation and labeling of cDNA.

MODES FOR CARRYING OUT THE INVENTION

Methods of the Invention

I. Methods for Methylation Analysis

The invention provides methods and kits for analyzing DNA methylation (including detecting and/or identifying methylated DNA sequences). In one aspect, the methods comprise use of an agent (such as an enzyme) that cleaves a base portion from a methylated nucleotide (such as 5-methylcytosine), whereby an abasic site is generated; cleavage of the phosphodiester backbone of the polynucleotide comprising the abasic site at the abasic site; and labeling at the abasic site, whereby labeled polynucleotide fragments are generated. In another aspect, the methods comprise use of an enzyme (such as cytosine deaminase in conjunction with uracil N glycosylase (UNG)) that cleaves a base portion from an unmethylated nucleotide, whereby an abasic site is generated, wherein the enzyme is not capable of cleaving a methylated nucleotide; cleavage of the phosphodiester backbone of the polynucleotide comprising the abasic site at the abasic site; and labeling at the abasic site, whereby labeled polynucleotide fragments are generated.

Generally, the polynucleotide comprising a methylated nucleotide (in some embodiments, suspected of comprising a methylated nucleotide) is fragmented and labeled at the abasic site (which is generated by cleavage of a base portion of the methylated nucleotide). Thus, the methods of the invention are useful for, e.g., detecting methylation (including presence and/or absence and/or quantity or level of methylation), identifying methylated polynucleotide sequences, isolating methylated polynucleotide sequences, identifying and/or isolating methylatable polynucleotide sequences, and other applications as described herein. The methods of the invention generate labeled polynucleotide fragments which are useful for, e.g., hybridization to a microarray and other uses described herein.

In one aspect, the methods involve the following steps: (a) contacting a polynucleotide comprising (in some embodiments, suspected of comprising) a methylated nucleotide with an agent capable of cleaving a base portion of the methylated nucleotide (i.e., cleaving a base portion of the methylated nucleotide), whereby an abasic site is generated; (b) cleaving the backbone of the polynucleotide comprising the abasic site at the abasic site; and (c) contacting the polynucleotide comprising the abasic site with an agent capable of labeling the abasic site (i.e., labeling the abasic site), whereby labeled polynucleotide fragments are generated.

In another aspect, the methods involve the following steps: (a) contacting a polynucleotide comprising (in some embodiments, suspected of comprising) a methylated nucleotide with an agent capable of cleaving a base portion of an unmethylated nucleotide (i.e., cleaving a base portion of the unmethylated nucleotide), whereby an abasic site is generated, wherein the agent is not capable of cleaving a methylated nucleotide; (b) cleaving the backbone of the polynucleotide comprising the abasic site at the abasic site; and (c) contacting the polynucleotide comprising the abasic site with an agent capable of labeling the abasic site (i.e., labeling the abasic site), whereby labeled polynucleotide fragments are generated.

In another aspect, the methods comprise the following steps: (a) contacting a polynucleotide comprising (in some embodiments, suspected of comprising) a methylated nucleotide with an enzyme capable of cleaving a base portion of an unmethylated nucleotide (i.e., cleaving a base portion of the unmethylated nucleotide), whereby an abasic site is generated, wherein the enzyme is not capable of cleaving a methylated nucleotide; (b) cleaving the backbone of the polynucleotide comprising the abasic site at the abasic site; and (c) contacting the polynucleotide comprising the abasic site with an agent capable of labeling the abasic site (i.e., labeling the abasic site), whereby labeled polynucleotide fragments are generated. In some embodiments, the enzyme is cytosine deaminase in conjunction with uracil DNA glycosylase.

In another aspect, the invention provides methods using the labeled and/or fragmented methylated polynucleotides, for, e.g., detection of methylation (including presence and/or absence and/or quantity or level of methylation), identification of methylated polynucleotide sequences, isolation of methylated polynucleotide sequences, characterization of methylated polynucleotide sequences, and other applications as described herein.

II. Methods for Labeling and Fragmenting a Polynucleotide Comprising a Cleavable Canonical Nucleotide, and Methods for Labeling a Polynucleotide Comprising a Cleavable Canonical Nucleotide The invention provides novel methods and kits for labeling and fragmenting a polynucleotide, and novel methods and kits for labeling a polynucleotide. These methods are suitable for, for example, generation of labeled polynucleotides, or labeled polynucleotide fragments, for use as hybridization targets. Generally, the polynucleotide is labeled at an abasic site present in the polynucleotide, and fragmented at an abasic site present in the polynucleotide (in embodiments involving fragmentation). The abasic site present in the polynucleotide is generally prepared by cleavage of a base portion of a cleavable canonical (interchangeably termed "canonical") nucleotide present in the polynucleotide.

Thus, in one aspect, the invention provides methods for labeling and fragmenting a polynucleotide. The methods generally comprise cleavage of a base portion of a canonical nucleotide present in a polynucleotide comprising the canonical nucleotide with an agent (such as an enzyme) capable of cleaving a base portion of the canonical nucleotide (whereby an abasic site is generated); cleavage of the phosphodiester backbone at the abasic site, and labeling at the abasic site, whereby labeled polynucleotide fragments are generated. In another aspect, the invention provides methods for labeling a polynucleotide. The methods generally comprise cleavage of a base portion of a canonical nucleotide present in a polynucleotide comprising the canonical nucleotide with an agent (such as an enzyme) capable of cleaving a base portion of the canonical nucleotide (whereby an abasic site is generated); and labeling at the site of incorporation of the canonical nucleotide (i.e., at the abasic site), whereby a labeled polynucleotide(s) is generated.

The polynucleotide comprising the canonical nucleotide (that is to be cleaved by the agent that cleaves a base portion of the canonical nucleotide) can be single stranded, double-stranded or partially double stranded. In some embodiments, the polynucleotide comprises a cDNA. In other embodiments, the polynucleotide comprises RNA, mRNA, genomic DNA, or synthetic DNA. In other embodiments, the polynucleotide comprises a cDNA library, a subtractive hybridization library, or a genomic library.

It is understood that a polynucleotide comprising a canonical nucleotide can be a multiplicity (from small to very large) of different polynucleotide molecules. Such populations can be related in sequence (e.g., members of a gene family or superfamily) or extremely diverse in sequence (e.g., generated from all mRNA, generated from all genomic DNA, etc.). Polynucleotides can also correspond to single sequences (which can be part or all of a known gene, including, e.g., a coding region, genomic region, gene locus, etc.).

A base portion of the canonical nucleotide is cleaved by an agent (such as an enzyme) capable of cleaving a base portion of a canonical nucleotide. Such agents are known in the art and described herein. In some embodiments, the agent capable of cleaving a base portion of a canonical nucleotide is cytosine deaminase (generally in conjunction with UNG), acidic conditions or treatment with an alkylating agent. In some embodiments, the agent is an enzyme. In other embodiments, the agent is a chemical agent. In still other embodiments, the agent is reaction conditions (e.g., acidic conditions).

In some embodiments, the invention provides methods wherein the cleavage of the base portion of the cleavable canonical nucleotide is under the same conditions (using the same agent) as the cleavage of the backbone at the abasic site, and labeling at the abasic site. In some embodiments, the reaction conditions are acidic reaction conditions (such as pH 3, pH 3.5 or pH 4). In still other embodiments, labeling and fragmentation (including cleavage of the base portion of the canonical nucleotide and cleavage of the phosphodiester backbone at an abasic site) are under the same conditions (using the same agent). In still other embodiments, the reaction conditions are acidic reaction conditions (such as pH 3, pH 3.5 or pH 4).

The methods of the invention involving cleavage of a cleavable canonical nucleotide include methods using the labeled polynucleotide fragments and labeled polynucleotides produced by the methods of the invention (so-called "applications"). The invention provides methods to characterize (for example, detect presence or absence of and/or quantify) a sequence of interest by analyzing the labeled and/or fragmented products by detection quantification methods such as those based on array technologies or solution phase technologies. In some embodiments, the invention provides methods of detecting the presence or absence of mutations. The invention provides methods of detection wherein detection correlates with presence, absence, sequence, and/or amount of polynucleotide. These detection methods apply to all methods described herein (based on cleavage of methylated nucleotides, unmethylated nucleotides, as well as canonical nucleotides).

In other embodiments, the invention provides methods of producing a hybridization target, hybridization to a hybridization probe; detection of the target hybridized to the probe; characterizing and/or quantitating nucleic acid, preparing a subtractive hybridization probe, comparative genomic hybridization, and determining a gene expression profile, using the labeled and/or fragmented nucleic acids generated by the methods of the invention.

The invention also provides methods for the generation of polynucleotides, or fragments thereof, immobilized to a substrate (surface). In some embodiments, the immobilized polynucleotide, or immobilized polynucleotide fragment (in embodiments involving fragmentation) is labeled according to the labeling methods described herein. These methods are suitable for, for example, the production of microarrays or tagged analytes.

The methods of the invention include methods using the immobilized polynucleotides, or immobilized polynucleotide fragments produced by the methods of the invention (so-called "applications"). In some embodiments, the invention provides methods of detecting nucleic acid sequence mutations.

The invention also provides methods to characterize (for example, detect presence or absence of and/or quantify) a sequence of interest using the immobilized polynucleotides, or fragments thereof.

In another embodiment, the invention provides methods of determining a gene expression profile, using the immobilized polynucleotides, or fragments thereof, generated by the methods of the invention.

General Techniques

The practice of the invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the invention can be generated using standard techniques known in the art.

DEFINITIONS

"Polynucleotide," or "nucleic acid," as used interchangeably herein, refer to polymers of nucleotides of any length, and include DNA. The nucleotides can be deoxyribonucleotides, modified nucleotides or bases, and/or their analogs, or any substrate that can be incorporated into a polymer by DNA polymerase. In embodiments involving methylation analysis, nucleotides include methylated nucleotides. A polynucleotide may comprise modified (altered) nucleotides, such as, for example, modification to the nucleotide structure and or modification to the phosphodiester backbone. As discussed herein modified nucleotide can be a canonical (cleavable) nucleotides, though, generally, a canonical nucleotide according to the methods for cleavage of a canonical nucleotide includes an unmodified base portion (i.e., unmodified adenine, cytosine, guanine and thymine base). It is understood, however, that modified nucleotides that are not (canonical) cleavable nucleotide under the reaction conditions used in the methods of the invention, if present, generally should not affect the ability of the polynucleotide to undergo cleavage of a base portion of the cleavable canonical nucleotide, such that an abasic site is generated, and/or cleavage of a phosphodiester backbone at an abasic site, such that fragments are generated, and/or immobilization of a polynucleotide (or fragment thereof) to a substrate, as described herein. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide (s). It is understood that internucleotide modifications may, e.g., alter the efficiency and/or kinetics of cleavage of the phosphodiester backbone (as when, for example a phosphodiester backbone is cleaved at an abasic site, as described herein). Further, any of the hydroxyl groups ordinarily present in the sugars may be replaced, for example, by phosphonate groups, phosphate groups, protected by standard protecting groups, or activated to prepare additional linkages to additional nucleotides. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including DNA. It is understood, however, that modified nucleotides and/or internucleotide linkages, if present, generally should not affect the ability of the polynucleotide to undergo cleavage of a base portion of a canonical nucleotide, such that an abasic site is generated, and/or the ability of a polynucleotide to undergo cleavage of a phosphodiester backbone at an abasic site, such that fragments are generated, and/or the ability of a polynucleotide to be immobilized at an abasic site (such as an abasic site at an end of a polynucleotide and/or an abasic site that is not at an end of a polynucleotide) to a surface, as described herein.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

A "primer," as used herein, refers to a nucleotide sequence (a polynucleotide), generally with a free 3'-OH group, that hybridizes with a template sequence (such as a template RNA, or a primer extension product) and is capable of promoting polymerization of a polynucleotide complementary to the template. A "primer" can be, for example, an oligonucleotide. It can also be, for example, a sequence of the template (such as a primer extension product or a fragment of an RNA template created following cleavage of a template RNA in an RNA-DNA complex by RNase H or other agent) that is hybridized to a sequence in the template itself (for example, as a hairpin loop), and that is capable of promoting nucleotide polymerization by DNA polymerase. Thus, a primer can be an exogenous (e.g., added) primer or an endogenous (e.g., template fragment) primer.

A "complex" is an assembly of components. A complex may or may not be stable and may be directly or indirectly detected. For example, as is described herein, given certain components of a reaction, and the type of product(s) of the reaction, existence of a complex can be inferred. For purposes of this invention, a complex is generally an intermediate with respect to the final polynucleotide fragments, labeled polynucleotide, labeled polynucleotide fragments, and/or immobilized polynucleotide or fragment thereof.

A "fragment" of a polynucleotide or oligonucleotide is a contiguous sequence of 2 or more bases. In other embodiments, a fragment (also termed "region" or "portion") is any of about 3, about 5, about 10, about 15, about 20, about 25, about 30 about 35 about 40, about 50, about 65, about 75, about 85, about 100, about 125, about 150, about 175, about 200, about 225, about 250, about 300, about 350, about 400, about 450, about 500, about 550, about 600, about 650 or more nucleotides in length. In some embodiments, the fragments can be at least about 3, about 5, about 10, about 15, about 20, about 25, about 30, about 35, about 40, about 50, about 65, about 75, about 85, about 100, about 125, about 150, about 175, about 200, about 225, about 250, about 300, about 350, about 400, about 450, about 500, about 550, about 600, about 650 or more nucleotides in length. In other embodiments, the fragments can be less than about 3, about 5, about 10, about 15, about 20, about 25, about 30 about 35 about 40, about 50, about 65, about 75, about 85, about 100, about 125, about 150, about 175, about 200, about 225, about 250, about 300, about 350, about 400, about 450, about 500, about 550, about 600, about 650 or more nucleotides in length. In some embodiments, these fragment lengths represent an average size in the population of fragments generated using the methods of the invention.

A "reaction mixture" is an assemblage of components, which, under suitable conditions, react to form a complex (which may be an intermediate) and/or a product(s).

"A", "an" and "the", and the like, unless otherwise indicated include plural forms. "A" fragment means one or more fragments. "A" methylated nucleotide means one or more methylated nucleotides. "An" enzyme means one or more than one enzyme.

"Comprising" means including in accordance with well-established principles of patent law (i.e., open language).

Conditions that "allow" an event to occur or conditions that are "suitable" for an event to occur, such as polynucleotide synthesis, cleavage of a base portion of a canonical nucleotide, cleavage of a base portion of a methylated nucleotide, cleavage of a phosphodiester backbone at an abasic site, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the polynucleotide sequence, temperature, and buffer conditions. These conditions also depend on what event is desired, such as polynucleotide synthesis, cleavage of a base portion of a canonical nucleotide, cleavage of a base portion of a methylated nucleotide, cleavage of a phosphodiester backbone at an abasic site, labeling an abasic site, immobilizing a polynucleotide fragment or a polynucleotide, etc.

"Microarray" and "array," as used interchangeably herein, comprise a surface with an array, preferably ordered array, of putative binding (e.g., by hybridization) sites for a biochemical sample (target) which often has undetermined characteristics.

The term "3'" generally refers to a region or position in a polynucleotide or oligonucleotide 3' (downstream) from another region or position in the same polynucleotide or oligonucleotide. "3'" may also refer to the 3' end of a polynucleotide or oligonucleotide.

The term "5'" generally refers to a region or position in a polynucleotide or oligonucleotide 5' (upstream) from another region or position in the same polynucleotide or oligonucleotide. "5'" may also refer to the 5' end of a polynucleotide or oligonucleotide.

The terms "3'-DNA portion," "3'-DNA region," "3'-RNA portion," and "3'-RNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide. The 3' most nucleotide(s) can be preferably from about 1 to about 50, more preferably from about 10 to about 40, even more preferably from about 20 to about 30 nucleotides. In some embodiments, a 3' portion can be any of at least about 1, 2, 3, 4, 5, 6, 7, 8, 10, 15, 20, 30, or 40 nucleotides. In some embodiments, a 3' portion can be about 1 to about 20 nucleotides, about 5 to about 20 nucleotides, or about 5 to about 50 nucleotides.

The terms "5'-DNA portion," "5'-DNA region," "5'-RNA portion," and "5'-RNA region," refer to the portion or region of a polynucleotide or oligonucleotide located towards the 5' end of the polynucleotide or oligonucleotide, and may or may not include the 5' most nucleotide(s) or moieties attached to the 5' most nucleotide of the same polynucleotide or oligonucleotide. The 5' most nucleotide(s) can be preferably from about 1 to about 50, more preferably from about 10 to about 40, even more preferably from about 20 to about 30 nucleotides. In some embodiments a 5' portion can be at least about any of 1, 2, 3, 4, 5, 6, 7, 8, 10, 15, 20, 30, or 40 nucleotides. In some embodiments, a 5' portion can be about 1 to about 20 nucleotides, about 5 to about 20 nucleotides, or about 5 to about 50 nucleotides.

As used herein in the context of methods for labeling and/or fragmenting a canonical nucleotide, "canonical" nucleotide means a nucleotide comprising one of the four common nucleic acid bases adenine, cytosine, guanine and thymine that are commonly found in DNA. The term also encompasses the respective deoxyribonucleosides, deoxyribonucleotides or 2'-deoxyribonucleoside-5'-triphosphates that contain one of the four common nucleic acid bases adenine, cytosine, guanine and thymine.

The term "analyte" as used herein refers to a substance to be detected or assayed by the method of the present invention, for example, a compound whose properties, location, quantity and/or identity is desired to be characterized. Typical analytes may include, but are not limited to proteins, peptides, nucleic acid segments, cells, microorganisms and fragments and products thereof, organic molecules, inorganic molecules, or any substance for which immobilization sites for binding partner(s) can be developed. As this disclosure clearly conveys, an analyte is a substrate.

As used herein, an "abasic site" refers to the site of a canonical nucleotide following treatment with an agent capable of effecting cleavage of a base portion of the canonical nucleotide (in embodiments relating to labeling and/or fragmentation of a polynucleotide comprising a canonical nucleotide), or the site of the methylated nucleotide following treatment with an agent capable of effecting cleavage of a base portion of the methylated nucleotide (in embodiments relating to labeling and/or fragmentation of a polynucleotide comprising a methylated nucleotide) or the site of the unmethylated nucleotide following treatment with an agent capable of effecting cleavage of a base portion of the methylated nucleotide (in embodiments relating to labeling and/or fragmentation of a polynucleotide comprising a methylated nucleotide, said methods comprising cleavage of a base portion of a unmethylated nucleotide. An abasic site (interchangeably termed "AP site") can comprise a hemiacetal ring and/or an aldehyde moiety, and lacks a base portion of the canonical nucleotide. As used herein, "abasic site" encompasses, in embodiments relating to labeling and/or fragmentation of a polynucleotide comprising a canonical nucleotide, any chemical structure remaining following treatment of a canonical nucleotide (present in a polynucleotide chain) with an agent (e.g., an enzyme, chemical reagent, heat, acidic conditions, and/or basic conditions) capable of effecting cleavage of a base portion of a canonical nucleotide, and, in embodiments relating to labeling and/or fragmentation of a polynucleotide comprising a methylated nucleotide, any chemical structure remaining following treatment of a methylated nucleotide (present in a polynucleotide chain) (or, in some embodiments, treatment of an unmethylated nucleotide) with an agent (e.g., an enzyme, chemical reagent, heat, acidic conditions, and/or basic conditions) capable of effecting cleavage of a base portion of a methylated nucleotide (or, in some embodiments, an unmethylated nucleotide). An abasic site may also occur in a natural polynucleotide, indicating damage to the polynucleotide.

As used herein, "labeling at an abasic site" means association of a label with, in embodiments relating to labeling and/or fragmentation of a polynucleotide comprising a canonical nucleotide, any chemical structure remaining following removal of a base portion (including the entire base) of a canonical nucleotide (present in a polynucleotide chain) by treatment with an agent (e.g., an enzyme, or heat)) capable of effecting cleavage of a base portion of a canonical nucleotide, or, in embodiments relating to labeling and/or fragmentation of a polynucleotide comprising a methylated nucleotide, treatment with an agent capable of effecting cleavage of a base portion of a methylated nucleotide (or, in some embodiments, an unmethylated nucleotide). In one embodiment, a reactive aldehyde form of a hemiacetal ring in an abasic site is labeled. In other embodiments involving cleavage of a base portion of a canonical nucleotide, the label associates with a chemical structure remaining following treatment of a canonical nucleotide (present in a polynucleotide chain) with an agent (e.g., an enzyme, or heat or basic conditions) capable of effecting cleavage of a base portion of a canonical nucleotide and treatment of polynucleotide comprising an abasic site with an agent capable of effecting cleavage of the backbone at the abasic site (as described herein), or, in embodiments involving cleavage of a base portion of a methylated nucleotide, the label associates with a chemical structure remaining following treatment of a methylated nucleotide (present in a polynucleotide chain) (in some embodiments, an unmethylated nucleotide) with an agent (e.g., an enzyme, or heat or basic conditions) capable of effecting cleavage of a base portion of a methylated nucleotide (in some embodiments, an unmethylated nucleotide) and treatment of polynucleotide comprising an abasic site with an agent capable of effecting cleavage of the backbone at the abasic site (as described herein).

As used herein, cleavage of a backbone (e.g. phosphodiester backbone) "at" an abasic site means cleavage of the phosphodiester linkage 3' to the abasic site or 5' to the abasic site, or both. As the disclosure herein conveys, "at" an abasic site refers to proximate or near location (such as immediately 3' or immediately 5'). In still other embodiments, more complex forms of cleavage are possible, for example, cleavage such that cleavage of the phosphodiester backbone and cleavage of (a portion of) the abasic site results.

As used herein, a "label" (interchangeably called a "detectable moiety") refers to a moiety that is associated or covalently linked with a polynucleotide (interchangeably called "labeling"). The labeled polynucleotide may be directly or indirectly detected, generally through a detectable signal. The detectable moiety (label) can be covalently attached (or associated) either directly or indirectly through a non-interfering linkage group with other moieties capable of specifically associating with one or more sites to be labeled. The detectable moiety (label) may be covalently linked or non-covalently associated as well as directly or indirectly associated.

Methods for Labeling and/or Fragmenting a Polynucleotide Comprising a Methylated Nucleotide The following are examples of the methods of the invention. It is understood that various other embodiments may be practiced, given the general description provided herein. For example, reference to using an agent capable of cleaving a base portion of the methylated nucleotide means that any of the agents capable of cleaving a base portion of the methylated nucleotide described herein may be used.

A. Methods for Labeling and Fragmenting a Polynucleotide Comprising a Methylated Nucleotide and Analyzing DNA Methylation The invention provides methods for analyzing DNA methylation (including detecting and/or identifying methylated DNA sequences). Generally, the methods comprise use of an agent (such as an enzyme) that cleaves a base portion from a methylated nucleotide (such as 5-methylcytosine), whereby an abasic site is generated; cleavage of the phosphodiester backbone of the polynucleotide comprising the abasic site at the abasic site; and labeling at the abasic site, whereby labeled polynucleotide fragments are generated. Generally, the polynucleotide comprising a methylated nucleotide (in some embodiments, suspected of comprising a methylated nucleotide) is fragmented and labeled at the abasic site (which is generated by cleavage of a base portion of the methylated nucleotide). Thus, the methods of the invention are useful for, e.g., detecting methylation (including presence and/or absence and/or quantity or level of methylation), identifying methylated polynucleotide sequences, isolating methylated polynucleotide sequences, identifying and/or isolating methylatable polynucleotide sequences, and other applications as described herein. The methods of the invention generate labeled polynucleotide fragments which are useful for, e.g., hybridization to a microarray and other uses described herein.

In one aspect, the methods involve the following steps: (a) contacting a polynucleotide comprising (in some embodiments, suspected of comprising) a methylated nucleotide with an agent capable of cleaving a base portion of the methylated nucleotide (i.e., cleaving a base portion of the methylated nucleotide), whereby an abasic site is generated; (b) cleaving the backbone of the polynucleotide comprising the abasic site at the abasic site; and (c) contacting the polynucleotide comprising the abasic site with an agent capable of labeling the abasic site (i.e., labeling the abasic site), whereby labeled polynucleotide fragments are generated.

Generally, native methylation status is analyzed (i.e., methylation status or pattern as exists in vivo, or substantially similar to the in vivo status or pattern), wherein the polynucleotide is directly harvested and/or isolated from a biological sample (such as a tissue or cell culture), though other embodiments are contemplated (including embodiments comprising detection and/or identification of methylatable sequences) in which the polynucleotide is from any source (i.e., genomic DNA, or a source other than genomic DNA) and the polynucleotide is methylated prior to labeling and fragmenting as described above). Thus, methylation status may be the result of in vivo processes, or of experimental manipulations (e.g., deliberate exposure to a putative DNA damaging agent, or a putative demethylating agent). The methods of the invention (i.e., the methods comprising cleavage of a base portion of a methylated nucleotide; cleavage of the backbone at the abasic site and/or labeling at the abasic site) specifically exclude methods comprising synthesis of a polynucleotide comprising a non-canonical nucleotide as disclosed in co-pending co-owned U.S. patent application Ser. No. 10/441,663 (publication no. 2004/0005614). Thus, the polynucleotide comprising a methylated nucleotide (or suspected of comprising a methylated nucleotide), as that term is used herein, does not encompass (specifically excludes) a polynucleotide comprising a non-canonical nucleotide, wherein the polynucleotide was generated by a method comprising synthesizing a polynucleotide comprising a non-canonical nucleotide from a template (i.e., such that the non-canonical nucleotide is incorporated during template-dependent synthesis of the polynucleotide comprising a non-canonical nucleotide.)

The polynucleotide to be analyzed for methylation status (e.g., the polynucleotide suspected of comprising a methylated nucleotide and/or the polynucleotide comprising a methylated nucleotide) may be any polynucleotide from which labeled polynucleotide fragments are desired to be produced, including double-stranded, partially double-stranded, and single-stranded nucleic acids from any source in purified or unpurified form, which can be DNA (dsDNA and ssDNA) or RNA, including tRNA, mRNA, rRNA, mitochondrial DNA and RNA, chloroplast DNA and RNA, DNA-RNA hybrids, or mixtures thereof, genes, chromosomes, the genomes of biological material such as plants, animals, humans, and fragments thereof (including fragments comprising hypermethylated CpG islands, centromeric regions, and other hypermethylated regions), though other embodiments are contemplated, as described herein. The polynucleotide can be known or unknown and may contain more than one sequence of interest, each of which may be the same or different from each other. The polynucleotide can be a subpopulation of nucleic acids, for example, a subtractive hybridization probe, total genomic DNA, or restriction fragments.

Obtaining and purifying nucleic acids use standard techniques in the art. Generally, the polynucleotide is DNA, though, as noted herein, the polynucleotide can comprise altered and/or modified nucleotides, internucleotide linkages, ribonucleotides, etc. As generally used herein, it is understood that "DNA" applies to polynucleotide embodiments. The polynucleotide suspected of comprising a methylated nucleotide can be processed or modified prior to analysis, for example, cleavage using restriction enzymes or other means known in the art, such as shearing, and using chemical or enzymatic methylation or demethylation as known in the art.

For simplicity, the polynucleotide comprising (or suspected of comprising) a methylated nucleotide is described as a single nucleic acid. It is understood that the polynucleotide is generally a population of polynucleotides (from a few to a multiplicity to a very large multiplicity of polynucleotides). It is further understood that a polynucleotide comprising a methylated nucleotide can be a multiplicity (from small to very large) of different polynucleotide molecules. Such populations can be related in sequence (e.g., member of a gene family or superfamily) or extremely diverse in sequence (such as all genomic DNA). Polynucleotides can also correspond to single sequence (which can be part or all of a known gene, for example a coding region, genomic portion, etc.). In some embodiments, the polynucleotide comprises a gene, a gene locus, a specific CpG dinucleotide, a CpG island, and/or a centromeric region.

For simplicity, individual steps of the labeling and fragmentation method are discussed herein. It is understood, however, that the steps may be performed simultaneously and/or in varied order, as discussed herein.

It is further understood that for convenience, methods involving cleavage of a base portion of a methylated nucleotide, and methods involving cleavage of a base portion of a non-methylated nucleotide (wherein the agent that cleaves a base portion of a nonmethylated nucleotide (interchangeably termed "unmethylated" nucleotide) is generally not capable of cleaving the base portion of a methylated nucleotide) (described below) are described separately. It is understood that the methods may be combined, performed separately, and/or performed sequentially.

1. Cleaving a Base Portion of a Methylated Nucleotide to Create an Abasic Site

In aspects involving cleavage of a base portion of a methylated nucleotide, the polynucleotide comprising a methylated nucleotide (in some embodiments, suspected of comprising a methylated nucleotide) is treated with an agent, such as an enzyme, capable of generally, specifically, or selectively cleaving a base portion of the methylated deoxyribonucleoside to create an abasic site. As used herein, "abasic site" encompasses any chemical structure remaining following removal of a base portion (including the entire base) of a methylated nucleotide with an agent capable of cleaving a base portion of a methylated nucleotide, e.g., by treatment of a methylated nucleotide (present in a polynucleotide chain) with an agent (e.g., an enzyme) capable of effecting cleavage of a base portion of a methylated nucleotide. In some embodiments, the agent (such as an enzyme) catalyzes hydrolysis of the bond between the base portion of the methylated nucleotide and a sugar in the methylated nucleotide to generate an abasic site comprising a hemiacetal ring and lacking the base (interchangeably called "AP" site), though other cleavage products are contemplated for use in the methods of the invention. Generally, the methods involving cleavage of a base portion of a methylated nucleotide are suitable for use with polynucleotides comprising a low frequency of methylated nucleotides (i.e., generally, not hypermethylated regions, such a CpG islands and the like), though other uses are contemplated.

The polynucleotide comprising (in some embodiments, suspected of comprising) a methylated nucleotide is treated with an agent, such as an enzyme, capable of generally, specifically, or selectively cleaving a base portion of the methylated deoxyribonucleoside to create an abasic site. As used herein, "abasic site" encompasses any chemical structure remaining following removal of a base portion (including the entire base) of a methylated nucleotide with an agent capable of cleaving a base portion of a methylated nucleotide, e.g., by treatment of a methylated nucleotide (present in a polynucleotide chain) with an agent (e.g., an enzyme, acidic conditions, or a chemical reagent) capable of effecting cleavage of a base portion of a methylated nucleotide. In some embodiments, the agent (such as an enzyme) catalyzes hydrolysis of the bond between the base portion of the methylated nucleotide and a sugar in the canonical nucleotide to generate an abasic site comprising a hemiacetal ring and lacking the base (interchangeably called "AP" site), though other cleavage products are contemplated for use in the methods of the invention.

In some embodiments, the methylated nucleotide is 5-methylcytosine. In some embodiments, 5-methylcytosine is present as a methylated CpG dinucleotide. The CpG dinucleotide may be fully or hemi-methylated. In other embodiments, the methylated nucleotide is 3-methyladenine. In other embodiments, the methylated nucleotide is 7-methyladenine and/or 3-methylguanine.

Suitable agents and reaction conditions for cleavage of base portions of methylated nucleotides are known in the art, and include: 5-methylcytosine DNA glycosylase (5-MCDG), which cleaves the base portion of 5-methylcytosine (5-MeC) from the DNA backbone (Wolffe et al., Proc. Nat. Acad. Sci. USA 96:5894-5896, 1999); 3-methyladenosine-DNA glycosylase I, which cleaves the base portion of 3-methyl adenosine from the DNA backbone (see, e.g. Hollis et al (2000) Mutation Res. 460: 201-210); and/or 3-methyladenosine DNA glycosylase II, which cleaves the base portion of 3-methyladenosine, 7-methylguanine, 7-methyladenosine, and/3-methylguanine from the DNA backbone. See McCarthy et al (1984) EMBO J. 3:545-550. Multifunctional and mono-functional forms of 5-MCDG have been described. See Zhu et al., Proc. Natl. Acad. Sci. USA 98:5031-6, 2001; Zhu et al., Nuc. Acid Res. 28:4157-4165, 2000; and Nedderrnann et al., J. B. C. 271:12767-74, 1996 (describing bifunctional 5-MCDG; Vairapandi & Duker, Oncogene 13:933-938, 1996; Vairapandi et al., J. Cell. Biochem. 79:249-260, 2000 (describing mono-functional enzyme comprising 5-MCDG activity). In some embodiments, 5-MCDG preferentially cleaves fully methylated polynucleotide sites (e.g., CpG dinucleotides), and in other embodiments, 5-MCDG preferentially cleaves a hemi-methylated polynucleotide. For example, mono-functional human 5-methylcytosine DNA glycosylase cleaves DNA specifically at fully methylated CpG sites, and is relatively inactive on hemimethylated DNA (Vairapandi & Duker, supra; Vairapandi et al., supra). By contrast, chick embryo 5-methylcytosine-DNA glycosylase has greater activity directed to hemimethylated methylation sites. In some embodiments, the activity of 5-MCDG is potentiated (increased or enhanced) with accessory factors, such as recombinant CpG-rich RNA, ATP, RNA helicase enzyme, and proliferating cell nuclear antigen (PCNA). See U.S. Patent Publication No. 20020197639 A1. One or more agents may be used. In some embodiments, the one or more agents cleave a base portion of the same methylated nucleotide. In other embodiments, the one or more agents cleave a base portion of different methylated nucleotides. Treatment with two or more agents may be sequential or simultaneous.

As is evident, in some embodiments, dUTP is generated as an intermediate and cleavage of a base portion of dUTP is necessary to generate the abasic site. Methods for cleaving a base portion of dUTP are known in the art. See, e.g., Lindahl, PNAS (1974) 71(9):3649-3653; Jendrisak, U.S. Pat. No. 6,190,865 B1; U.S. Pat. No. 5,035,996; U.S. Pat. No. 5,418, 149; Sartori et al (2002) EMBO J 21:3182-3191. Thus, in some embodiments, an agent that cleaves a base portion of a methylated nucleotides (such as an enzyme, such as 5-MCDG) is used in conjunction with UNG to generate an abasic site from the methylated nucleotide. As used herein, "in conjunction" encompasses simultaneous treatment (e.g., when 5-MCDG and UNG cleavage occurs in the same reaction mixture) and/or treatment at different times (e.g., when 5-MCDG and UNG treatment is conducted sequentially).

In some embodiments, the agent that cleaves the base portion of the methylated nucleotide is the same agent that cleaves a phosphodiester backbone at the abasic site.

In some embodiments, cleavage of the base portion of the methylated nucleotides is general, specific or selective cleavage (in the sense that the agent (such as an enzyme) capable of cleaving a base portion of a methylated nucleotide generally, specifically or selectively cleaves the base portion of a particular methylated nucleotide), whereby about any of 98%, 95%, 90%, 85%, or 80% of the base portions cleaved are base portions of methylated nucleotides. However, extent of cleavage can be less. Thus, reference to specific cleavage is exemplary.

As noted herein, for convenience, cleavage of a base portion of a methylated nucleotide (whereby an abasic site is generated) has been described as a separate step. It is understood that this step may be performed simultaneously with cleavage of the backbone at an abasic site (fragmentation) and/or labeling at an abasic site.

It is understood that the frequency (or spacing) of abasic sites in the resulting polynucleotide comprising an abasic site (following cleavage of a base portion of a methylated nucleotide, and thus the average size of fragments generated using the methods of the invention (i.e., following cleavage of a phosphodiester backbone at an abasic site), is controlled by variables known in the art, including: frequency of methylated nucleotide(s) in the polynucleotide (or other measures of nucleotide content of a sequence, such as average G-C content), length of the polynucleotide comprising a methylated nucleotide, and the reaction conditions used during generation of abasic site, as is further discussed herein. In some embodiments, polynucleotide are additionally cleaved using other means (e.g., restriction digestion, mechanical cleavage) before or after cleavage and labeling at an abasic site using the methods of the invention.

2. Cleaving the Backbone at the Abasic Site of the Polynucleotide Comprising an Abasic Site and Labeling at the Abasic Site The backbone of the polynucleotide is cleaved at the abasic site, and the abasic site is labeled, whereby labeled polynucleotide fragments are generated. It is understood that cleavage of the backbone and labeling can be performed in any order, or simultaneously. For convenience, however, these reactions are described as separate steps.

i. Cleaving the Backbone at the Abasic Site of the Polynucleotide Comprising an Abasic Site Following generation of an abasic site, the backbone of the polynucleotide is cleaved at the abasic site (i.e., the site generated following cleavage of the base portion of the methylated nucleotide) with an agent capable of effecting cleavage of the backbone at the abasic site. Cleavage at the backbone (also termed "fragmentation") results in at least two fragments (depending on the number of abasic sites present in the polynucleotide comprising an abasic site, and the extent of cleavage).

Suitable agents (for example, an enzyme, a chemical and/or reaction conditions such as heat) capable of cleavage of the backbone at an abasic site are well known in the art, and include: heat treatment and/or chemical treatment (including basic conditions, acidic conditions, alkylating conditions, or amine mediated cleavage of abasic sites, (see e.g., co-pending co-owned U.S. patent application Ser. No. 10/441,663; McHugh and Knowland, Nucl. Acids Res. (1995) 23(10): 1664-1670; Bioorgan. Med. Chem (1991) 7:2351; Sugiyama, Chem. Res. Toxicol. (1994) 7: 673-83; Horn, Nucl. Acids. Res., (1988) 16:11559-71), and use of enzymes that catalyze cleavage of polynucleotides at abasic-sites, for example AP endonucleases (also called "apurinic, apyrimidinic endonucleases") (e.g., E. coli Endonuclease IV, available from Epicentre Tech., Inc, Madison Wis.), E. coli endonuclease III or endonuclease IV, E. coli exonuclease III in the presence of calcium ions. See, e.g. co-pending co-owned U.S. patent application Ser. No. 10/441,663; Lindahl, PNAS (1974) 71(9):3649-3653; Jendrisak, U.S. Pat. No. 6,190,865 B1; Shida, Nucleic Acids Res. (1996) 24(22):4572-76; Srivastava, J. Biol Chem. (1998) 273(13):21203-209; Carey, Biochem. (1999) 38:16553-60; Chem Res Toxicol (1994) 7:673-683. As used herein "agent" encompasses reaction conditions such as heat. In one embodiment, the AP endonuclease, E. coli endonuclease IV, is used to cleave the phosphodiester backbone at an abasic site. In another embodiment, cleavage is with an amine, such as N,N'-dimethylethylenediamine. See, e.g. McHugh and Knowland, supra.

Generally, cleavage is between the nucleotide immediately 5' to the abasic residue and the abasic residue, or between the nucleotide immediately 3' to the abasic residue and the abasic residue (though, as explained herein, 5' or 3' cleavage of the phosphodiester backbone may or may not result in retention of the phosphate group 5' or 3' to the abasic site, respectively, depending on the fragmentation agent used). As is well known in the art, cleavage can be 5' to the abasic site (such as endonuclease IV treatment which generally results in cleavage of the backbone at a location immediately 5' to the abasic site between the 5'-phosphate group of the abasic residue and the deoxyribose ring of the adjacent nucleotide, generating a free 3' hydroxyl group on the adjacent nucleotide), such that an abasic site is located at the 5' end of the resulting fragment. Cleavage can also be 3' to the abasic site (e.g., cleavage between the deoxyribose ring and 3'-phosphate group of the abasic residue and the deoxyribose ring of the adjacent nucleotide, generating a free 5' phosphate group on the deoxyribose ring of the adjacent nucleotide), such that an abasic site is located at the 3' end of the resulting fragment. Treatment under basic conditions or with amines (such as N,N'-dimethylethylenediamine) results in cleavage of the phosphodiester backbone immediately 3' to the abasic site. In addition, more complex forms of cleavage are also possible, for example, cleavage such that cleavage of the phosphodiester backbone and cleavage of (a portion of) the abasic site results. For example, under certain conditions, cleavage using chemical treatment and/or thermal treatment may comprise a β-elimination step which results in cleavage of a bond between the abasic site deoxyribose ring and its 3' phosphate, generating a reactive α,β-unsaturated aldehyde which can be labeled or can undergo further cleavage and cyclization reactions. See, e.g. Sugiyama, Chem. Res. Toxicol. (1994) 7: 673-83; Horn, Nucl. Acids. Res., (1988) 16:11559-71. It is understood that more than one method of cleavage can be used, including two or more different methods which result in multiple, different types of cleavage products (e.g., fragments comprising an abasic site at the 3' end, and fragments comprising an abasic site at the 5' end).

Generally, cleavage of the backbone at an abasic site is general, specific or selective cleavage (in the sense that the agent (such as an enzyme) capable of cleaving the backbone at an abasic site specifically or selectively cleaves the backbone at an abasic site), whereby greater than about 98%, about 95%, about 90%, about 85%, or about 80% of the cleavage is at an abasic site. However, extent of cleavage can be less. Thus, reference to specific cleavage is exemplary. In some embodiments, specific or selective cleavage is desirable for control of the fragment size in the methods of generating labeled polynucleotide fragments of the invention. In some embodiments, reaction conditions can be selected such that the cleavage reaction is performed in the presence of a large excess of reagents and allowed to run to completion. In other embodiments, extent of cleavage can be less, such that polynucleotide fragments are generated comprising an abasic site at an end and an abasic site(s) within or internal to the polynucleotide fragment (i.e., not at an end). As disclosed herein, polynucleotide fragments comprising internal abasic sites are useful e.g., in embodiments involving immobilization of a labeled polynucleotide (wherein one abasic site is used for immobilization and another abasic site(s) are labeled at an abasic site).

As noted herein, the approximate or average size of the fragments (following cleavage of an abasic site, and cleavage of the backbone at the abasic site as described herein) is controlled by variables known in the art, including: frequency of cleavable nucleotides in the polynucleotide (in some embodiments involving methylation analysis, frequency of methylated nucleotides), or other measures of nucleotide content of a sequence, such as average G-C content), length of the polynucleotide, and the reaction conditions used during generation of abasic site and cleavage of the backbone at the abasic site. In some embodiments, polynucleotide are additionally cleaved using other means (e.g., restriction digestion, mechanical cleavage) before or after cleavage and labeling at an abasic site using the methods of the invention. Generally, suitable fragment sizes are about 5, 10, 15, 20, 25, 30, 40, 50, 65, 75, 85, 100, 123, 150, 175, 200, 225, 250, 300, 350, 400, 450, 500, 550, 600, 650 or more, such as 1 kb, 2 kb, 3 kb, 4 kb, 5 kb or more nucleotides in length. In some embodiments, the fragment is about 200 nucleotides, about 100 nucleotides, or about 50 nucleotides in length. In another embodiment, the size of a population of fragments is about 50 to 200 nucleotides. It is understood that the fragment size may be approximate, particularly when populations of fragments are generated, because the frequency and spacing of abasic sites (which relates to the fragment size following cleavage) will vary from template to template and also between copies of the same template, due to representation of the methylated nucleotide, reactions conditions selected for generation of abasic sites, and reaction conditions selected for fragmentation. Thus, in some embodiments, fragments generated from same starting material (such as a single polynucleotide template) may have different (and/or overlapping) sequence, while still having the same approximate size or size range.

Following cleavage of the polynucleotide backbone at the abasic site, every fragment will comprise one abasic site (if cleavage is completely efficient), except for either the 5'- or 3'-most fragment, which may lack an abasic site depending on the cleavage agent. If the cleavage is 5' to the abasic site, the 5' most fragment will not comprise an abasic site. If cleavage is 3' to the abasic site, the 3' most fragment will not comprise an abasic site.

It is understood that the preceding disclosure regarding cleavage of the backbone at the abasic site is applicable to embodiments involving cleavage of the backbone at the abasic site wherein the abasic site was generated by cleavage of a cleavable canonical nucleotide with an agent capable of cleaving a base portion of a canonical nucleotide, as described infra.

ii. Labeling the Abasic Site and Detection

The abasic site is labeled, whereby a polynucleotide (or polynucleotide fragment) comprising a label is generated. In some embodiments, a polynucleotide fragment comprising an abasic site is contacted with an agent capable of labeling at the abasic site; whereby labeled fragments of the polynucleotide are generated. As used herein, a "label" (interchangeably called a "detectable moiety") is attached to or associated with a polynucleotide, such that the polynucleotide comprising an abasic site is attached to or associated with a label.

Thus, in some embodiments, the label attaches to or associates with a chemical structure remaining following treatment of a methylated nucleotide (present in a polynucleotide chain) with an agent (e.g., an enzyme, or acidic conditions, or a chemical reagent) capable of effecting cleavage of a base portion of the methylated nucleotide. In embodiments involving fragmentation, the label attaches to or associates with any chemical structure remaining following treatment of the methylated nucleotide (present in a polynucleotide chain) with an agent (e.g., an enzyme, or acidic conditions, or a chemical reagent) capable of effecting cleavage of a base portion of the methylated nucleotide (in embodiments involving cleavage of a methylated nucleotide), and following treatment with an agent capable of cleaving the backbone at the abasic site. In one embodiment, the label covalently bonds with a reactive aldehyde form of a hemiacetal ring in an abasic site. In some embodiments, labeling "at" an abasic site encompasses labels that bind to an abasic site, but do not bind to the intact (uncleaved) methylated nucleotide (in embodiments involving cleavage of a methylated nucleotide) whether incorporated or present as a single methylated nucleotide). In some embodiments, labeling "at" an abasic site specifically excludes labels that attach (e.g., covalently bind) to a phosphate group of a nucleotide (or polynucleotide) or a phosphate group of an abasic site. In some embodiments, labeling "at" an abasic site specifically excludes labels that attach or associate at the 3' position of the sugar. In still other embodiments, labeling "at" an abasic site specifically excludes a label comprised of a phosphine. As made clear from the disclosure herein, "label" refers to any component of a labeling system.

It is understood that cleavage of the phosphodiester backbone at the abasic site, and labeling at an abasic site can be performed in any order, or simultaneously.

The label can be detectable, or the label can be indirectly detected, for example as when the label (attached at an abasic residue) is covalently or non-covalently associated with another moiety which is itself detected. For example, biotin can be attached to the label capable of associating with the abasic site. In another example, an antibody (that can be detectably labeled) binds the label that is attached at the abasic site. In some embodiments, the label comprises an organic molecule, a hapten, or a particle (such as a polystyrene bead). In some embodiments, the label is detected using antibody binding, biotin binding, or via fluorescence or enzyme activity. In some embodiments, the detectable signal is amplified.

Generally, labeling at an abasic site is general, specific, or selective labeling (in the sense that the agent capable of labeling at an abasic site specifically or selectively labels the abasic site), whereby greater than about 98%, about 95%, about 93%, about 90%, about 85%, or about 80% of the labels bind abasic sites. However, extent of labeling can be less. Thus, reference to specific labeling is exemplary. In some embodiments, reaction conditions are selected such that the reaction in which the abasic site(s) are labeled can run to completion.

In some embodiments, labeled polynucleotide fragments are produced which each comprise a single label (to the extent that cleavage of the phosphodiester backbone is generally complete, in the sense that many or essentially all of the polynucleotide fragments comprise a single abasic site). This aspect is useful in quantitating level of hybridization, because signal is proportional to number of bound fragments, and does not relate to the length of the hybridizing fragment or the number of labels per fragment. Thus, hybridization intensity can generally be directly compared, regardless of fragment length. In another embodiment, labeled fragments are produced which comprise a labeled abasic site at an end (such as the 3' end and/or the 5' end) and a labeled internal abasic site.

Methods and reaction conditions for labeling abasic sites are known in the art. See, e.g., co-pending co-owned U.S. patent application Ser. No. 10/441,663. For example, a common functional group exposed in an abasic site (and therefore suitable for use in labeling) is the highly reactive aldehyde form of the hemiacetal ring which can be covalently attached to or noncovalently associated with a label using reaction conditions that are known in the art. Many labels comprise substituted hydrazines or hydroxylamines which readily form imine bonds with aldehydes, for example, 5-(((2-(carbohydrazino)-methyl)thio)acetyl)aminofluorescein, aminooxyacetyl hydrazide (FARP). See Makrigiorgos, PCT Publication No. WO 00/39345. The stable oxime formed by this compound can be detected directly by fluorescence or the signal can be amplified using an antibody-enzyme conjugate. See, e.g., Srivastava, J. Biol. Chem. (1998) 273(33): 21203-209; Makrigiorgos, Int J. Radiat. Biol. (1998) 74(1):99-109; Makrigiorgos, U.S. Pat. No. 6,174,680 B1; Makrigiorgos, WO 00/39345. Suitable sidechains (present on the substrate) to react with the aldehyde (of the abasic site) include at least the following: substituted hydrazines, hydrazides, or hydroxylamines (which readily form imine bonds with aldehydes), and the related semicarbazide and thiosemicarbazide groups, and other amines which can form stable carbon-nitrogen double bonds, that can catalyze simultaneous cleavage and binding (see Horn, Nucl. Acids. Res., (1988) 16:11559-71), or can be coupled to form stable conjugates, e.g. by reductive amination. Other methods for attaching a reactive group present in an abasic site to a reactive group present on a label are known in the art. In another example, the abasic site may be chemically modified, then the modified abasic site covalently attached to or non-covalently associated with a suitable reactive group on a substrate. For example, the aldehyde (in the abasic site) can be oxidized or reduced (using methods known in the art), then covalently immobilized to a substrate using, e.g., reductive amination or various oxidative processes.

Other suitable reagents are known in the art, e.g., fluorescein aldehyde reagents. See, e.g., Boturyn (1999) Chem. Res. Toxicol. 12:476-482. See, also, Adamczyk (1998) Bioorg. Med. Chem. Lett. 8(24):3599-3602; Adamczyk (1999) Org. Lett. 1(5):779-781; Kow (2000) Methods 22(2):164-169; Molecular Probes Handbook, Section 3.2 (www.probes.com). For example, detectable moieties comprising aminooxy groups can be used. See, Boturyn, supra. The aminooxy group readily reacts with the highly reactive aldehyde form of the hemiacetal ring of an abasic site. In one embodiment, the label comprising an aminooxy reactive group is N-(aminooxyacetyl)-N'-(D-biotinoyl) hydrazine, trifluoroacetic acid salt (ARP) (available from Molecular Probes, Eugene Oreg., catalog No. A-10550). See, e.g., Kubo et al., Biochem 31:3703-3708 (1992); Ide et al., Biochem. 32:8276-8283 (1993).

In yet another example, labels comprising a hydrazide linker can be converted to an aminooxy (interchangeably termed "hydroxylamine") derivative, then used to label abasic sites as described herein. In one embodiment, the label comprises an aminooxy derivatized Alexa Fluor 555 reagent as disclosed in co-pending U.S. patent application Ser. No. 10/441,663, Use of the aminooxy-derivatized Alexa Fluor 555 resulted in greater labeling efficiency, as well as increased fluorescence as compared to labeling with unmodified Alexa Fluor 555 hydrazide (Order No. A-20501, Molecule Probes, Eugene Oreg.).

In another example, the abasic site may be chemically modified (before, during or after cleavage of the phosphodiester backbone as described herein), then the modified abasic site detected directly or indirectly. For example, fluorescent cadaverine can be incorporated into an abasic site as described in Horn (Nucl. Acids. Res., (1988) 16:11559-71). In another example, the abasic site may be chemically modified by reaction with NHBA (0-4-nitrobenzyl hydroxylamine), then the NBHA-modified abasic site is detected with an antibody that specifically binds to the NBHA-modified abasic sites. See Kow et al, PCT Publication No. WO 92/07951 (1992).

In another example, the abasic site may be labeled with an antibody (such as a monoclonal or polyclonal antibody or antigen binding fragment). Methods for detecting specific antibody binding are well known in the art.

In another example, the aldehyde and/or hemiacetal ring may itself be detected, as when, for example, detectable signal is generated using chemical or electrochemical reactions specific to those chemical structures, including for example, oxidation reactions, enzymes with dehydrogenase or oxidase activity, and the like. In another example, many aldehydes are substrates for enzymes, such that a detectable product is generated in the presence of the aldehyde. For example, dehydrogenases typically couple oxidation of an aldehyde with reduction of NAD+ which can be detected spectrophotometrically. In another example, glucose oxidases generate hydrogen peroxide in the presence of sugar aldehydes. Hydrogen peroxide is readily detectable by coupling to horseradish peroxidase with suitable substrates. Thus, the invention provides methods for detecting an abasic site.

Methods of signal detection are known in the art: Signal detection may be visual or utilize a suitable instrument appropriate to the particular label used, such as a spectrometer, fluorimeter, or microscope. For example, where the label is a radioisotope, detection can be achieved using, for example, a scintillation counter, or photographic film as in autoradiography. Where a fluorescent label is used, detection may be by exciting the fluorochrome with the appropriate wavelength of light and detecting the resulting fluorescence, such as by microscopy, visual inspection or photographic film, fluorometer, CCD cameras, scanner and the like. Where enzymatic labels are used, detection may be by providing appropriate substrates for the enzyme and detecting the resulting reaction product. For example, many substrates of horseradish peroxidase, such as o-phenylenediamine, give colored products. Simple colorimetric labels can usually be detected by visual observation of the color associated with the label; for example, conjugated colloidal gold is often pink to reddish, and beads appear the color of the bead. Instruments suitable for high sensitivity detection are known in the art.

It is understood that the polynucleotide or polynucleotide fragments can be additionally labeled using other methods known in the art.

Labeled polynucleotide fragments can be immobilized to a substrate, as described herein.

It is understood that the preceding disclosure regarding labeling at the abasic site is applicable to embodiments involving labeling at the abasic site wherein the abasic site was generated by cleavage of a cleavable canonical nucleotide with an agent capable of cleaving a base portion of a canonical nucleotide, as described infra.

B. Methods for Labeling a Polynucleotide Comprising a Methylated Nucleotide

The invention provides methods for generating labeled nucleic acid(s).

Generally, the methods comprise use of an agent (such as an enzyme) that cleaves a base portion from a methylated nucleotide (such as 5-methylcytosine), whereby an abasic site is generated; and labeling at the a basic site, whereby labeled polynucleotides are generated. Generally, the polynucleotide comprising a methylated nucleotide (in some embodiments, suspected of comprising a methylated nucleotide) is labeled at the abasic site (which is generated by cleavage of a base portion of the methylated nucleotide). The methods of the invention generate labeled polynucleotides which are useful for, e.g., hybridization to a microarray and other uses described herein. The methods of the invention are suitable for multiplexing.

The methods involve the following steps; (a) contacting a polynucleotide comprising (in some embodiments, suspected of comprising) a methylated nucleotide with an agent capable of cleaving a base portion of the methylated nucleotide (i.e., cleaving a base portion of the methylated nucleotide), whereby an abasic site is generated; and (b) contacting the polynucleotide comprising the abasic site with an agent capable of labeling the abasic site (i.e., labeling the abasic site), whereby labeled polynucleotides are generated.

It is understood that labeled polynucleotides may be cleaved using other means (i.e. other means than cleavage at an abasic site as described herein, e.g., restriction digestion, mechanical cleavage) before or after labeling at an abasic site using the methods of the invention. In some embodiments, the methods involving labeling of a polynucleotide comprising a methylated nucleotide are suitable for multiplex analysis involving hybridization to an array.

1. Cleaving a Base Portion of a Methylated Nucleotide to Create an Abasic Site

The polynucleotide comprising a methylated nucleotide (in some embodiments, suspected of comprising a methylated nucleotide) is treated with an agent, such as an enzyme, capable of generally, specifically, or selectively cleaving a base portion of the methylated deoxyribonucleoside to create an abasic site, as described herein.

2. Labeling the Abasic Site and Detection

The abasic site is labeled, whereby a polynucleotide comprising a label is generated, as described herein.

C. Methods for Fragmenting a Polynucleotide Comprising a Methylated Nucleotide

The methods involve the following steps: (a) contacting a polynucleotide comprising (in some embodiments, suspected of comprising) a methylated nucleotide with an agent capable of cleaving a base portion of the methylated nucleotide (i.e., cleaving a base portion of the methylated nucleotide), whereby an abasic site is generated; and (b) cleaving the backbone of the polynucleotide comprising the abasic site at the abasic site, whereby polynucleotide fragments are generated.

1. Cleaving a Base Portion of a Methylated Nucleotide to Create an Abasic Site

The polynucleotide comprising a methylated nucleotide (in some embodiments, suspected of comprising a methylated nucleotide) is treated with an agent, such as an enzyme, capable of generally, specifically, or selectively cleaving a base portion of the methylated deoxyribonucleoside to create an abasic site, as described herein.

2. Cleaving the Backbone at the Abasic Site of the Polynucleotide Comprising an Abasic Site and Labeling at the Abasic Site The backbone of the polynucleotide is cleaved at the abasic site, and the abasic site is labeled, whereby polynucleotide fragments are generated, as described herein.

D. Methods for Labeling and Fragmenting a Polynucleotide Comprising a Methylated Nucleotide Using an Enzyme that Cleaves a Base Portion of a Nonmethylated Nucleotide In another aspect, the invention comprises use of an enzyme (such as cytosine deaminase in conjunction with uracil N deglycosylase (UNG)) that cleaves a base portion from an unmethylated nucleotide, whereby an abasic site is generated, wherein the enzyme is not capable of cleaving a methylated nucleotide; cleavage of the phosphodiester backbone of the polynucleotide comprising the abasic site at the abasic site; and labeling at the abasic site, whereby labeled polynucleotide fragments are generated. Generally, the polynucleotide comprising a methylated nucleotide (in some embodiments, suspected of comprising a methylated nucleotide) is fragmented and labeled at the abasic site (which is generated by cleavage of a base portion of the non-methylated nucleotide). Thus, the methods of the invention are useful for, e.g., detecting methylation (including presence and/or absence and/or quantity or level of methylation), identifying methylated polynucleotide sequences, isolating methylated polynucleotide sequences, identifying and/or isolating methylatable polynucleotide sequences, and other applications as described herein. The methods of the invention generate labeled polynucleotide fragments which are useful for, e.g., hybridization to a microarray and other uses described herein.

The methods comprise the following steps: (a) contacting a polynucleotide comprising (in some embodiments, suspected of comprising) a methylated nucleotide with an enzyme capable of cleaving a base portion of an unmethylated nucleotide (i.e., cleaving a base portion of the unmethylated nucleotide), whereby an abasic site is generated, wherein the enzyme is not capable of cleaving a methylated nucleotide; (b) cleaving the backbone of the polynucleotide comprising the abasic site at the abasic site; and (c) contacting the polynucleotide comprising the abasic site with an agent capable of labeling the abasic site (i.e., labeling the abasic site), whereby labeled polynucleotide fragments are generated. In some embodiments, the enzyme is cytosine deaminase in conjunction with uracil DNA glycosylase.

1. Cleaving a Base Portion of an Unmethylated Nucleotide

In another aspect, the invention comprises use of an enzyme (such as cytosine deaminase in conjunction with uracil DNA glycosylase) that cleaves a base portion of an unmethylated nucleotide, wherein the enzyme is not capable of cleaving a methylated nucleotide; cleavage of the phosphodiester backbone of the polynucleotide comprising the abasic site at the abasic site; and labeling at the abasic site, whereby labeled polynucleotide fragments are generated.

Generally, the methods involve the following steps: (a) contacting a polynucleotide comprising (in some embodiments, suspected of comprising) a methylated nucleotide with an agent (such as an enzyme) capable of cleaving a base portion of an unmethylated nucleotide (i.e., cleaving a base portion of the unmethylated nucleotide), whereby an abasic site is generated, wherein the agent (such as an enzyme) is not capable of cleaving the methylated nucleotide; (b) cleaving the backbone of the polynucleotide comprising the abasic site at the abasic site; and (c) contacting the polynucleotide comprising the abasic site with an agent capable of labeling the abasic site (i.e., labeling the abasic site), whereby labeled polynucleotide fragments are generated.

In some embodiments, the enzyme is cytosine deaminase. See Sohail et al, NAR 2003, 31: 2990-94. Cytosine deaminase catalyzes the deamination of cytosine, such that dUTP is generated. Cleavage of a base portion of dUTP is necessary to generate the abasic site. Thus, the invention encompasses use of (a) an agent (such as cytosine deaminase) that modifies a nucleotide (such as dCTP), whereby dUTP is generated, in conjunction with (b) an agent (such as an enzyme, such as UNG) that cleaves a base portion of dUTP, whereby an abasic site is generated. Methods for cleaving a base portion of dUTP are known in the art. See, e.g., Lindahl, PNAS (1974) 71(9):3649-3653; Jendrisak, U.S. Pat. No. 6,190,865 B1; U.S. Pat. No. 5,035,996; U.S. Pat. No. 5,418,149; Sartori et al (2002) EMBO J 21:3182-3191. As used herein, "in conjunction" encompasses simultaneous treatment (e.g., when cytosine deaminase and UNG cleavage occurs in the same reaction mixture) and/or treatment at different times (e.g., when cytosine deaminase and UNG treatment is conducted sequentially).

In some embodiments, the agent that cleaves the base portion of the unmethylated nucleotide is the same agent that cleaves a phosphodiester backbone at the abasic site.

Generally, cleavage of the base portion of the unmethylated nucleotides is general, specific or selective cleavage (in the sense that the agent (such as an enzyme) capable of cleaving a base portion of an unmethylated nucleotide generally, specifically or selectively cleaves the base portion of a particular unmethylated nucleotide), and generally, specifically and selectively does not cleave the base portion of the methylated nucleotide, whereby about any of 98%, 95%, 90%, 85%, or 80% of the base portions cleaved are base portions of unmethylated nucleotides. However, extent of cleavage can be less. Thus, reference to specific cleavage is exemplary. In some embodiments, the methylated nucleotide is 5-methylcytosine and the unmethylated nucleotide is cytosine.

As noted herein, for convenience, cleavage of a base portion of a unmethylated nucleotide (whereby an abasic site is generated) has been described as a separate step. It is understood that this step may be performed simultaneously with cleavage of the backbone at an abasic site (fragmentation) and/or labeling at an abasic site.

It is understood that the frequency (or spacing) of abasic sites in the resulting polynucleotide comprising an abasic site (following cleavage of a base portion of a unmethylated nucleotide, and thus the average size of fragments generated using the methods of the invention (i.e., following cleavage of a phosphodiester backbone at an abasic site), is controlled by variables known in the art, including: frequency of unmethylated nucleotide(s) in the polynucleotide (or other measures of nucleotide content of a sequence, such as average G-C content), length of the polynucleotide comprising a unmethylated nucleotide, and the reaction conditions used during generation of abasic site, as is further discussed herein (such as presence of a methylation binding protein, and/or presence of a DNA binding protein). In some embodiments, polynucleotide are additionally cleaved using other means (e.g., restriction digestion, mechanical cleavage) before or after cleavage and labeling at an abasic site using the methods of the invention.

It is understood that the methods involving cleavage of a base portion of an unmethylated nucleotide relate to and comprise use of a polynucleotide with native methylation status, i.e., a polynucleotide in which methylation status or pattern exists in vivo, as described herein. Specifically excluded are labeling and/or fragmentation methods comprising synthesis of a polynucleotide comprising a non-canonical nucleotide as disclosed in co-pending co-owned U.S. patent application Ser. No. 10/441,663 (publication no. 2004/0005614).

Generally, the methods involving cleavage of a nonmethylated nucleotide (but not cleavage of the corresponding methylated nucleotide) are suitable for use with polynucleotide templates that are heavily methylated (hypermethylated), though other polynucleotide templates are suitable for use in the methods of the invention. Methods involving cleavage in the presence of methyl binding proteins and/or DNA binding proteins are further described herein.

In some embodiments, the polynucleotide comprising methylated nucleotide is contacted with a methyl binding agent, such as a methyl binding antibody, and/or a methyl binding protein, prior to and/or during cleavage of the base portion of the unmethylated nucleotide. Binding with a methyl binding agent protects the portion of the polynucleotide bound from labeling and fragmentation (including cleavage of a nonmethylated nucleotide). For example, when using an enzyme for cleavage of the base, binding of the enzyme to a methylated nucleotide base or activity of the enzyme towards a methylated nucleotide, may be prevented by binding to the methyl binding agent. Thus, the methods generally produce polynucleotide fragments comprising a methylated nucleotide that are suitable for further analysis, such as by hybridization to a microarray. The methods are generally suitable, e.g., for the analysis of hypermethylated samples, where methods involving cleavage at a methylated nucleotide may result in excessive fragmentation. In some embodiments, the methods are useful for selectively fragmenting a non-hypermethylated sequence in the polynucleotide of interest, such that hypermethylated sequences may be isolated from the reaction mixture and further analyzed (including sequencing and/or cloning and/or hybridization to a microarray).

Antibodies that bind methylated nucleotides are known in the art. See, e.g., U.S. Patent Publication No. 2002/0197639; Erlanger and Beiser (PNAS, 52:68, 1964); Sano et al., (Biochemica et Biophysica Acta, 951:157, 1988); PCT Publication No. WO 99/10540 published on Mar. 4, 1999; Mizugaki et al (1996) Biol Pharm. Bull. 19:1537-40 (describing antibodies that recognize 5-methylcytosine) and Tohuku J. Exp Med. 1986, 149(2):151-161. Methyl binding proteins are also known in the art. See, e.g, Ballestar et al (2001) Eur J Biochem. 268; 1-6. As is well known in the art, a methyl binding protein (also termed methylation binding protein or MBP)

encompasses proteins that bind methylated nucleotides as well as proteins that bind a region including a methylated nucleotide.

In other embodiments, the polynucleotide comprising a methylated nucleotide is contacted with a polynucleotide (e.g. DNA) binding protein, such as a transcription factor, regulatory protein, and other DNA binding proteins, prior to cleavage of the base portion of the unmethylated nucleotide. The polynucleotide binding protein, e.g. a transcription factor, protects the bound portion of the polynucleotide from cleavage, thus generating a labeled and fragmented polynucleotide comprising the binding site of the particular DNA binding protein.

In some embodiments, methylation status may be compared in the presence or absence or methylation binding agents and/or other polynucleotide binding proteins. As further described herein, comparison of methylation status is useful to compare samples from, e.g., different stages of development, and/or different disease states (such as a control (normal) sample and a sample from diseased tissue).

2. Cleaving the Backbone at the Abasic Site of the Polynucleotide Comprising an Abasic Site Following generation of an abasic site, the backbone of the polynucleotide is cleaved at the abasic site (i.e., the site generated following cleavage of the base portion of the canonical nucleotide) with an agent capable of effecting cleavage of the backbone at the abasic site, as described herein.

3. Labeling the Abasic Site and Detection

The abasic site is labeled, whereby a polynucleotide (or polynucleotide fragment) comprising a label is generated as described herein. In some embodiments, a polynucleotide fragment comprising an abasic site is contacted with an agent capable of labeling at the abasic site; whereby labeled fragments of the polynucleotide are generated as described herein.

E. Applications Using the Labeling and/or Fragmentation Methods for Analysis of DNA Methylation The methods and compositions of the invention can be used for a variety of purposes. For purposes of illustration, methods of producing a hybridization probe or target characterizing and/or quantitating nucleic acid, preparing a subtractive hybridization probe, detection (using the hybridization probe), and determining methylation status, using the labeled and/or fragmented nucleic acids generated by the methods of the invention, are described.

1. Methods for Characterizing Methylated Polynucleotides

The labeled and/or fragmented nucleic acids obtained by the methods of the invention are amenable to further characterization.

The labeled and/or fragmented nucleic acids (i.e., products of any of the methods for labeling and/or fragmenting a polynucleotide comprising a methylated nucleotide described herein), can be analyzed using, for example, probe hybridization techniques known in the art, such as Southern and Northern blotting, and hybridizing to probe arrays. They can also be analyzed by electrophoresis-based methods, such as differential display and size characterization, which are known in the art, e.g., capillary electrophoresis and gel electrophoresis using a sequencing gel.

In one embodiment, the methods of the invention are utilized to generate labeled and/or fragmented nucleic acids, and analyze the labeled and/or fragmented nucleic acids by contact with a probe.

In one embodiment, the methods of the invention are utilized to generate labeled and/or fragmented nucleic acids which are analyzed (for example, detection and/or quantification) by contacting them with, for example, microarrays (of any suitable substrate, which includes glass, chips, plastic), beads, or particles, that comprise suitable probes such as cDNA and/or oligonucleotide probes. Thus, the invention provides methods to characterize (for example, detect and/or quantify and/or identify) a labeled and/or fragmented nucleic acid by analyzing the labeled products, for example, by hybridization of the labeled products to, for example, probes immobilized at, for example, specific locations on a solid or semi-solid substrate, probes immobilized on defined particles (including beads, such as Bead Array, Illumina), or probes immobilized on blots (such as a membrane), for example arrays, or arrays of arrays. Immobilized probes include immobilized probes generated by the methods described herein, and also include at least the following microarrays: cDNA and synthetic oligonucleotides, which can be synthesized directly on the substrate. In some embodiments, the microarray is an Affymetrix Gene Chip array, an Agilent oligonucleotide array, or Amersham CodeLink array, or other high density or low density oligonucleotide or cDNA array, including genome or focused arrays. The identity of the probes provides characterization of the sequence identity of the products, and thus by extrapolation can also provide characterization of the identity of the polynucleotide comprising a methylated nucleotide (termed "template") from which the products were prepared. Thus, it is evident that polynucleotides comprising a methylated nucleotide may be identified using the methods of the invention.

Other methods of analyzing labeled products are known in the art, such as, for example, by contacting them with a solution comprising probes, followed by extraction of complexes comprising the labeled products and probes from solution. The identity of the probes provides characterization of the sequence identity of the products, and thus by extrapolation can also provide characterization of the identity of a template from which the products were prepared. In addition, hybridization of the labeled products is detectable, and the amount of labels that are detected is proportional to the amount of the labeled products prepared from a specific polynucleotide comprising a methylated nucleotide. This measurement is useful for, for example, measuring the relative amount (quantity, extent) of methylated species in a sample. The amount of labeled products (as indicated by, for example, detectable signal associated with the label) hybridized at defined locations on an array is indicative of the detection and/or quantification of the corresponding methylated polynucleotide species in the sample.

In another aspect, the invention provides methods for detecting methylated polynucleotides, including detecting presence or absence or quantity (level and/or extent) of methylation in a polynucleotide sample (which may comprise one or a multiplicity, a large multiplicity or a very large multiplicity of polynucleotides comprising a methylated nucleotide (in some embodiments, suspected of comprising a methylated polynucleotide), including essentially all genomic DNA. In some embodiments, presence or absence or quantity of methylation is determined by hybridizing the labeled and/or fragmented polynucleotides (generated using any of the methods for labeling and/or fragmenting methylated polynucleotides described herein) to a polynucleotide (probe) of defined sequence (which may be immobilized, for example, on a microarray), as described further herein. In some embodiments, the microarray is a cDNA microarray. In some embodiments, the microarray is an Affymetrix Gene Chip array, an Agilent oligonucleotide array, or Amersham CodeLink array, or other high density or low density oligonucleotide or cDNA array, including genome or focused arrays. It is understood that amount of labeled and/or fragmented nucleic acids produced (and thus the amount of product) may be determined using quantitative and/or qualitative methods. Determining amount of labeled and/or fragmented nucleic acids includes determining whether labeled and/or fragmented nucleic acids are present or absent. Thus, amount or extent of methylation includes information relating to absence of methylation. "Absent" or "absence" of product, and "lack of detection of product" as used herein includes insignificant, or de minimus levels.

As described above, labeled and/or fragmented nucleic acids can be detected and quantified by various methods, as described herein and/or known in the art. Determination of the amount of methylated polynucleotide of interest present in a sample, as determined by quantifying products (for example labeled and/or fragmented products) of the methods described herein, provides for determination of the methylation status of the sample source. It is understood that presence or absence or quantity of methylation may be determined for one polynucleotide of interest, a multiplicity of polynucleotides, a large multiplicity, or a very large multiplicity of polynucleotides (including all or essentially all genomic DNA). In some embodiments, presence or absence or quantity (extent or pattern) of methylation is determined for a specific polynucleotide sequence. In other embodiments, presence or absence or quantity is determined for a multiplicity, a large multiplicity or a very large multiplicity of polynucleotide sequences. Polynucleotide sequences (for which methylation analysis is desired) may be known (e.g., a particular locus, genomic region, CpG island, CpG dinucleotide, etc.) or may be unknown or unidentified polynucleotide sequences.

In another aspect, the invention provides methods for isolating, enriching and/or identifying methylated polynucleotides. The methods of the invention are utilized to generate labeled and/or fragmented nucleic acids which are isolated, enriched and or identified. In some embodiments, labeled and/or fragmented polynucleotides are physically captured (for example, by binding to probes in solution or microarray), and captured polynucleotide products are isolated and or enriched. In other embodiments, labeled and/or fragmented polynucleotide products are identified via hybridization to a known probe or other means for characterizing the sequence thereof.

2. Comparison of Methylation Status

The labeled and/or fragmented nucleic acids generated according to the methods of the invention are also suitable for analysis for the detection of any alteration in methylation status (e.g., presence or absence or quantity, extent and/or pattern) in the template polynucleotide sequence (from which the labeled and/or fragmented nucleic acids are synthesized), as compared to a reference nucleic acid sequence which is identical to the template nucleic acid sequence other than the alteration in methylation status, if any.

Accordingly, the invention provides methods of comparing methylation status in a sample, said method comprising: (a) generating labeled and/or fragmented from at least one polynucleotide template in the sample using any of the methods described herein; and (b) determining amount of labeled polynucleotide or fragments thereof of each polynucleotide template, wherein each said amount is indicative of amount of each polynucleotide template in the sample.

The methods are useful in a wide variety of molecular diagnostics, and especially in the study of essentially any cell (including a single cell) or cell population. A cell or cell population (e.g. a tissue) may be from, for example, blood, brain, spleen, bone, heart, vascular, lung, kidney, pituitary, endocrine gland, embryonic cells, tumors, or the like. Comparison of methylation status is also useful for comparing a control (normal) sample to a test sample, including test samples collected at different times, including before, after, and/or during development, a treatment, and the like.

3. Comparative Hybridization

In another aspect, the invention provides methods for comparative hybridization (such as comparative genomic hybridization), said method comprising: (a) preparing a first population of labeled polynucleotides or fragments thereof from a first template polynucleotide sample using any of the methods described herein; (b) comparing hybridization of the first population to at least one probe with hybridization of a second population of labeled polynucleotides or fragments thereof. In still other embodiments, the at least one probe is provided as a microarray. In some embodiments, the first and second population comprises detectably different labels. In other embodiments, the second population of labeled polynucleotides, or fragments thereof, are prepared from a second polynucleotide sample using any of the methods described herein. In some embodiments, step (b) of comparing comprises determining amount of said products, whereby the amount of the first and second polynucleotide templates is quantified.

In some embodiments, comparative hybridization comprises preparing a first population of labeled polynucleotides (which can be polynucleotide fragments) according to any of the methods described herein. A second population of labeled polynucleotides (to which the first population is desired to be compared) is prepared from a second genomic DNA template. The first and second population may be hybridized to a single array (in which case, detectably different labels are generally used) or hybridized to different arrays (in which case the labels may be the same or different). Hybridization of the first and second populations is detected and compared.

Methods for Labeling and Fragmenting Polynucleotides Comprising a Cleavable Canonical Nucleotide, and Methods for Labeling a Polynucleotide Comprising a Cleavable Canonical Nucleotide A. Methods for Labeling and Fragmenting Polynucleotides Comprising a Cleavable Canonical Nucleotide The invention provides methods for generating labeled fragments of a polynucleotide comprising a cleavable canonical nucleotide (interchangeably termed "canonical nucleotide"). In some aspects, namely the RNA context, a canonical nucleotide includes a nucleotide comprising the base uracil (U) (as well as respective forms such as ribonucleoside, etc.).

The methods generally comprise cleavage of a base portion of a canonical nucleotide present in a polynucleotide comprising the canonical nucleotide with an agent capable of cleaving a base portion of the canonical nucleotide; and cleavage of the phosphodiester backbone of the polynucleotide comprising the abasic site at the abasic site; and labeling at the abasic site, whereby labeled nucleic acid fragments are generated. Generally, the polynucleotide comprising a canonical nucleotide is fragmented and labeled at the abasic site (generated by cleavage of a base portion of a canonical nucleotide). Thus, the frequency of abasic sites generated by cleavage of the base portion of the canonical nucleotide generally relates to and determines the size range of the labeled fragments produced from the polynucleotide. The methods of the invention generate labeled nucleic acid fragments, which are useful for, for example, hybridization to a microarray and other uses described herein.

The methods involve the following steps: (a) contacting a polynucleotide comprising a canonical nucleotide with an agent capable of cleaving a base portion of the canonical nucleotide (i.e., cleaving a base portion of the canonical nucleotide), whereby an abasic site is created; (b) cleaving the backbone of the polynucleotide comprising the abasic site at the abasic site; and (c) contacting the polynucleotide comprising the abasic site with an agent capable of labeling the abasic site (i.e., labeling the abasic site), whereby labeled polynucleotide fragments are generated.

For simplicity, individual steps of the labeling and fragmentation method are discussed below. It is understood, however, that the steps may be performed simultaneously and/or in varied order, as discussed herein.

In some embodiments, an abasic site is generated at about every 5, 10, 15, 20, 25, 30, 40, 50, 65, 75, 85, 100, 123, 150, 175, 200, 225, 250, 300, 350, 400, 450, 500, 550, 600, 650 or more nucleotides apart. In one embodiment, the abasic site is generated about every 200 nucleotides, about every 100 nucleotide, or about every 50 nucleotide. In another embodiment, the abasic site is generated about every 50 to about 200 nucleotides.

The frequency (or spacing) of abasic sites in the resulting polynucleotide comprising an abasic site (following cleavage of a base portion of a canonical nucleotide, and thus the average size of fragments generated using the methods of the invention (i.e., following cleavage of a phosphodiester backbone at an abasic site), is controlled by variables known in the art, including: frequency of canonical nucleotide(s) in the polynucleotide (or other measures of nucleotide content of a sequence, such as average G-C content), and the reaction conditions used during generation of abasic site, as is further discussed herein. The reaction conditions can be empirically determined, for example, by assessing average fragment size generated using the methods of the invention taught herein. In some embodiments, about any of 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 98%, or more canonical bases are cleaved.

The polynucleotide comprising a canonical nucleotide may be any template from which labeled polynucleotide fragments are desired to be produced, including double-stranded, partially double-stranded, and single-stranded nucleic acids from any source in purified or unpurified form, which can be DNA (dsDNA and ssDNA) or RNA, including tRNA, mRNA, rRNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof. Obtaining and purifying nucleic acids use standard techniques in the art. RNAs can be obtained and purified using standard techniques in the art. A DNA template (including genomic DNA template) can be transcribed into RNA form, which can be achieved using methods disclosed in Kurn, U.S. Pat. No. 6,251,639 B1, and by other techniques (such as expression systems) known in the art. RNA copies of genomic DNA would generally include untranscribed sequences generally not found in mRNA, such as introns, regulatory and control elements, etc. DNA copies of an RNA template can be synthesized using methods described in Kurn, U.S. Patent Publication No. 2003/0087251 A1 or other techniques known in the art). Synthesis of polynucleotide from a DNA-RNA hybrid can be accomplished by denaturation of the hybrid to obtain a ssDNA and/or RNA, cleavage with an agent capable of cleaving RNA from an RNA/DNA hybrid, and other methods known in the art. The template can be only a minor fraction of a complex mixture such as a biological sample and can be obtained from various biological materials by procedures well known in the art. The template can be known or unknown and may contain more than one desired specific nucleic acid sequence of interest, each of which may be the same or different from each other. The template DNA can be a sub-population of nucleic acids, for example, a subtractive hybridization probe, total genomic DNA, restriction fragments, a cDNA library, cDNA prepared from total mRNA, a cloned library, or amplification products of any of the templates described herein. In some cases, the initial step of the synthesis of the complement of a portion of a template nucleic acid sequence is template denaturation. The denaturation step may be thermal denaturation or any other method known in the art, such as alkali treatment.

For simplicity, the polynucleotide comprising a canonical nucleotide is described as a single nucleic acid. It is understood that the polynucleotide can be a single polynucleotide, or a population of polynucleotides (from a few to a multiplicity to a very large multiplicity of polynucleotides). It is further understood that a polynucleotide comprising a canonical nucleotide can be a multiplicity (from small to very large) of different polynucleotide molecules. Such populations can be related in sequence (e.g., member of a gene family or superfamily) or extremely diverse in sequence (e.g., generated from all mRNA, generated from all genomic DNA, etc.). Polynucleotides can also correspond to single sequence (which can be part or all of a known gene, for example a coding region, genomic portion, etc.). Methods, reagents, and reaction conditions for generating specific polynucleotide sequences and multiplicities of polynucleotide sequences are known in the art.

Generally, the polynucleotide is DNA, though, as noted herein, the polynucleotide can comprise altered and/or modified nucleotides, internucleotide linkages, ribonucleotides, etc. As generally used herein, it is understood that "DNA" applies to polynucleotide embodiments. In some aspects, namely the RNA context, a canonical nucleotide includes a nucleotide comprising the base uracil (U) (as well as respective forms such as ribonucleoside, etc.).

Polynucleotides may be generated or isolated, e.g., from a sample. Methods for preparing polynucleotide are well known in the art. Methods for synthesizing polynucleotides, e.g., single and double stranded DNA, from a template are well known in the art, and include, for example, single primer isothermal amplification (SPIA™), Ribo-SPIA™, PCR, reverse transcription, primer extension, limited primer extension, replication (including rolling circle replication), strand displacement amplification (SDA), nick translation, multiple displacement amplification (MDA). See, e.g., Kurn, U.S. Pat. No. 6,251,639 B1; Kurn, PCT Publication No. WO 02/00938; Kurn, U.S. Patent Publication No. 2003/0087251 A1; Mullis, U.S. Pat. No. 4,582,877; Wallace, U.S. Pat. No. 6,027,923; U.S. Pat. Nos. 5,508,178; 5,888,819; 6,004,744; 5,882,867; 5,710,028; 6,027,889; 6,004,745; 5,763,178; 5,011,769; see also Sambrook (1989) "Molecular Cloning: A Laboratory Manual", second edition; Ausebel (1987, and updates) "Current Protocols in Molecular Biology"; Mullis, (1994) "PCR: The Polymerase Chain Reaction". One or more methods known in the art can be used to synthesize polynucleotides. Suitable methods include methods that result in one single- or double-stranded polynucleotide comprising a canonical nucleotide (for example, reverse transcription, production of double stranded cDNA, a single round of DNA replication), as well as methods that result in multiple single stranded or double stranded copies or copies of the complement of a template (for example, single primer isothermal amplification or Ribo-SPIA™ or PCR). In one embodiment, a single-stranded polynucleotide comprising a canonical nucleotide is synthesized using single primer isothermal amplification. See Kurn, U.S. Pat. No. 6,251,639 B1.

1. Cleaving a Base Portion of a Canonical Nucleotide to Create an Abasic Site

The polynucleotide comprising a canonical nucleotide is treated with an agent, such as an enzyme, capable of generally, specifically, or selectively cleaving a base portion of the canonical deoxyribonucleoside to create an abasic site. As used herein, "abasic site" encompasses any chemical structure remaining following removal of a base portion (including the entire base) of a canonical nucleotide with an agent capable of cleaving a base portion of a nucleotide. In some embodiments, the agent (such as an enzyme) catalyzes hydrolysis of the bond between the base portion of the canonical nucleotide and a sugar in the canonical nucleotide to generate an abasic site comprising a hemiacetal ring (in some embodiments, comprising an aldehyde moiety) and lacking the base (interchangeably called "AP" site), though other cleavage products are contemplated for use in the methods of the invention. Suitable agents and reaction conditions for cleavage of base portions of cleavable canonical nucleotides are known in the art, and include the agents shown in Table 1.

TABLE 1

| Canonical nucleotide | Agent | Mechanism | Reference |
|---|---|---|---|
| dC | bisulfite | dC + $HSO_3^-$ → dU → AP site** | U.S. Pat. No. 6,017,704 |
| dC | Cytosine deaminase | dC → dU → AP site** | Sohail et al, NAR 2003, 31: 2990-94. |
| dG | Acidic conditions; alkylation (e.g., dimethyl sulfate treatment) | dG → AP site | |

**UNG catalyzes dU → AP (abasic site).

One or more agents may be used. In some embodiments, the one or more agents cleave a base portion of the same canonical nucleotide. In other embodiments, the one or more agents cleave a base portion of different canonical nucleotides. In some embodiments, the agent is an enzyme. In other embodiments, the agent is a chemical agent. In still other embodiments, the agent is a reaction condition (such as presence of acidic conditions).

As is evident, in some embodiments dUTP is generated as an intermediate and cleavage of a base portion of dUTP is necessary to generate the abasic site. Methods for cleaving a base portion of dUTP are known in the art. See, e.g., Lindahl, PNAS (1974) 71(9):3649-3653; Jendrisak, U.S. Pat. No. 6,190,865 B1; U.S. Pat. No. 5,035,996; U.S. Pat. No. 5,418,149. For example, in some embodiments, the enzyme cytosine deaminase is used to deaminate dCTP, whereby dUTP is generated. UNG is then used to cleave the base portion of dUTP, whereby an abasic site is generated. Thus, in some embodiments, cytosine deaminase is used in conjunction with UNG to generate an abasic site from the canonical nucleotide dCTP. As used herein, "in conjunction" encompasses simultaneous treatment (e.g., when cytosine deaminase and UNG cleavage occurs in the same reaction mixture) and/or treatment at different times (e.g., when cytosine deaminase and UNG treatment is conducted sequentially).

As is evident, in some embodiments, different agents cleave the base portion of the canonical nucleotide and cleave the phosphodiester backbone at the abasic site. In other embodiments, the agent that cleaves the base portion of the canonical nucleotide is the same agent that cleaves a phosphodiester backbone at the abasic site. In some embodiments, fragmentation and labeling is performed under acidic conditions (in some embodiments, at pH 2-5; in some embodiments, pH 3-3.5). Example 1 exemplifies reaction conditions suitable for efficient labeling and fragmentation under acidic conditions. In still other embodiments, ARP labeling and fragmentation are performed under substantially similar reaction conditions.

In some embodiments, cleavage of base portions of canonical nucleotides is general, specific or selective cleavage (in the sense that the agent (such as an enzyme) capable of cleaving a base portion of a canonical nucleotide generally, specifically or selectively cleaves the base portion of a particular canonical nucleotide), whereby about 90%, about 85%, or about 80% of the base portions cleaved are base portions of canonical nucleotides. However, extent of cleavage can be less. Thus, reference to specific cleavage is exemplary.

As noted herein, for convenience, cleavage of a base portion of a canonical nucleotide (whereby an abasic site is generated) has been described as a separate step. It is understood that this step may be performed simultaneously with synthesis of the polynucleotide comprising a canonical nucleotide (in embodiments involving synthesis of the polynucleotide comprising the cleavable canonical nucleotide), cleavage of the backbone at an abasic site (fragmentation) and/or labeling at an abasic site. Example 1 exemplifies the use of acidic conditions for cleavage of a canonical nucleotide (generally, dGTP) and cleavage of the phosphodiester backbone at the abasic site.

In some embodiments involving synthesis of the polynucleotide comprising the canonical nucleotide, the polynucleotide comprising a canonical nucleotide is purified following synthesis of the canonical polynucleotide (to eliminate, for example, residual free canonical nucleotides that are present in the reaction mixture). In other embodiments, there is no intermediate purification between the synthesis of the polynucleotide comprising the canonical nucleotide and subsequent steps (such as cleavage of a base portion of the canonical nucleotide and cleavage of a phosphodiester backbone at the abasic site).

2. Cleaving the Backbone at the Abasic Site of the Polynucleotide Comprising an Abasic Site Following generation of an abasic site, the backbone of the polynucleotide is cleaved at the abasic site (i.e., the site generated following cleavage of the base portion of the canonical nucleotide) with an agent capable of effecting cleavage of the backbone at the abasic site, as described herein.

3. Labeling the Abasic Site and Detection

The abasic site is labeled, whereby a polynucleotide (or polynucleotide fragment) comprising a label is generated as described herein. In some embodiments, a polynucleotide fragment comprising an abasic site is contacted with an agent capable of labeling at the abasic site; whereby labeled fragments of the polynucleotide are generated as described herein.

B. Methods for Labeling Nucleic Acids Comprising a Cleavable Canonical Nucleotide The invention provides methods for generating labeled nucleic acid(s). The methods generally comprise cleavage of a base portion of a canonical nucleotide present in a polynucleotide with an agent capable of cleaving the base portion of the canonical nucleotide; and labeling the abasic site, whereby labeled polynucleotide(s) is generated. Generally, the polynucleotide comprising a canonical nucleotide is labeled at the site of the canonical nucleotide in the polynucleotide (following generation of an abasic site by cleavage of a base portion of the canonical nucleotide). The methods of the invention generate labeled polynucleotide(s), which are useful for, for example, hybridization to a microarray and other uses described herein.

The methods involve the following steps: (a) contacting the polynucleotide comprising a canonical nucleotide with an agent capable of cleaving a base portion of the canonical nucleotide, whereby an abasic site is created; and (b) labeling the abasic site in the polynucleotide comprising the abasic site, whereby labeled polynucleotide(s) is generated.

For simplicity, individual steps of the labeling methods are discussed below. It is understood, however, that the steps may be performed simultaneously and in varied order, as discussed herein.

In some embodiments, an basic site is generated at about every 5, 10, 15, 20, 25, 30, 40, 50, 65, 75, 85, 100, 123, 150, 175, 200, 225, 250, 300, 350, 400, 450, 500, 550, 600, 650 or more nucleotides apart. In one embodiment, the abasic site is generated about every 200 nucleotides, about every 100 nucleotide, or about every 50 nucleotide. In another embodiment, the abasic site is generated about every 50 to about 200 nucleotides.

The frequency (or spacing) of abasic sites in the resulting polynucleotide comprising an abasic site (following cleavage of a base portion of a canonical nucleotide, and thus the average size of fragments generated using the methods of the invention (i.e., following cleavage of a phosphodiester backbone at a canonical nucleotide), is controlled by variables known in the art, including: frequency of canonical nucleotide(s) in the polynucleotide (or other measures of nucleotide content of a sequence, such as average G-C content), and the reaction conditions used during generation of abasic site, as is further discussed herein. The reaction conditions can be empirically determined, for example, by assessing average fragment size generated using the methods of the invention taught herein. In some embodiments, about any of 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or more canonical bases are cleaved.

1. Cleaving a Base Portion of a Canonical Nucleotide to Create an Abasic Site

The polynucleotide comprising a canonical nucleotide is treated with an agent, such as an enzyme, capable of generally, specifically, or selectively cleaving a base portion of the canonical deoxyribonucleoside to create an abasic site, as described herein.

2. Labeling the Abasic Site and Detection

The abasic site is labeled, whereby a polynucleotide comprising a label is generated, as described herein.

Methods for Preparing Polynucleotides (or Fragments Thereof) and Immobilization on a Substrate The invention provides methods for generating polynucleotides or polynucleotide fragments and immobilization of the fragments on a substrate (interchangeably termed a "surface", herein). The methods generally comprise immobilizing the polynucleotide, or fragments thereof, on a substrate, wherein the polynucleotide or fragment thereof is immobilized at the abasic site, wherein the polynucleotide, or fragment thereof, is generated using any of the methods described herein. Optionally, the polynucleotide comprising an abasic site can be labeled at an abasic site according to the labeling methods described herein. The methods of the invention generate polynucleotides, and fragments thereof, immobilized on a substrate, for example, a microarray. In some embodiments, one or more abasic site(s) are labeled (as described herein) and one or more abasic site(s) are immobilized to a substrate.

The methods involve the following steps: immobilizing a polynucleotide (or polynucleotide fragments) on a substrate, wherein the polynucleotide is immobilized to the substrate at the abasic site; wherein the polynucleotide (or polynucleotide fragment) comprising an abasic site is generated by any of the methods described herein.

After generation of the polynucleotide comprising an abasic site, the polynucleotide (or polynucleotide fragment, if the backbone is cleaved) is immobilized to a substrate at the abasic site. In embodiments involving cleavage of the backbone at an abasic site (whereby fragments of the synthesized nucleic acid are generated), the cleaved fragments are immobilized to a substrate at the cleaved abasic site. Immobilizing a polynucleotide(s) is useful, for example, to tag an analyte, or to create a microarray. Single stranded polynucleotides (including polynucleotide fragments) are particularly suitable for preparing microarrays comprising the single stranded polynucleotides. Single stranded polynucleotide fragments (in embodiments involving cleavage of the phosphodiester backbone at an abasic site) are advantageous, because the orientation of the fragment with respect to the substrate (upon which the fragment is immobilized) can be controlled by selection of the method used to cleave the phosphodiester backbone, such that an abasic site is positioned at the 3' end of a fragment or at the 5' end of a fragment. Immobilizing polynucleotides in a defined orientation (e.g., at the 3' end, at the 5' end) enhances hybridization of complementary oligonucleotides, and permits a higher density of immobilization.

The polynucleotide comprising the abasic site is immobilized to a substrate as follows: generally, reagents are used that are capable of covalently or non-covalently attaching a reactive group present in the abasic site to a reactive group present on a substrate. For example, a common functional group exposed in an abasic site (and therefore suitable for use in labeling) is the aldehyde of the hemiacetal ring which can be covalently or noncovalently attached to a reactive group on a suitable substrate using reaction conditions that are known in the art. Suitable sidechains (present on the substrate) to react with the aldehyde (of the abasic site) include at least the following: substituted hydrazines, hydrazides, or hydroxylamines (which readily form imine bonds with aldehydes), and the related semicarbazide and thiosemicarbazide groups, and other amines which can form stable carbon-nitrogen double bonds, that can catalyze simultaneous cleavage and binding (see Horn, Nucl. Acids. Res., (1988) 16:11559-71), or can be coupled to form stable conjugates, e.g. by reductive amination.

The substrate to which the polynucleotide is to be immobilized can be functionalized with suitable reactive groups using methods known in the art. For example, a solid or semi-solid substrate (e.g., silicon or glass slide) can be coated with polymers (e.g., polyacrylamide, dextran, acrylamide, or latex) comprising hydrazine, hydrazide, or amine derivatized substrates (e.g. semicarbazides). Methods for functionalizing substrates with suitable reactive groups are known in the art, and disclosed in, for example, Luktanov, U.S. Pat. No. 6,339,147; Van Ness, U.S. Pat. No. 5,667,976; Bangs Laboratories, Inc. TechNote 205 (available at bangslabs.com); Ghosh, Anal. Biochem (1989) 178:43-51; O'Shannessy, Anal. Biochem. (1990) 191:1-8; Wilchek, Methods Enzymol. (1987)

138:429-442; Baumgartner, Anal. Biochem. (1989) 181:182-189; Zalipsky, Bioconjugate Chem. (1995) 6: 150-165, and references cited therein.

Methods and reaction conditions for performing these reactions are known in the art. See, e.g. Luktanov, U.S. Pat. No. 6,339,147; Van Ness, U.S. Pat. No. 5,667,976; Bangs Laboratories, Inc. TechNote 205 (available at bangslabs.com); Ghosh, Anal. Biochem (1989) 178:43-51; O'Shannessy, Anal. Biochem. (1990) 191:1-8; Wilchek, Methods Enzymol. (1987) 138:429-442; Baumgartner, Anal. Biochem. (1989) 181:182-189; Zalipsky, Bioconjugate Chem. (1995) 6: 150-165, and references cited therein. It is appreciated that similar chemistry is described herein with respect to the methods of labeling an abasic site (i.e., embodiments in which a reactive group in the abasic site is covalently or non-covalently attached to a suitable reactive group on a label). See, e.g., Srivastava, J. Biol. Chem. (1998) 273(33): 21203-209; Makrogiorgos, Int J. Radiat. Biol. (1998) 74(1): 99-109; Makrigiorgos, U.S. Pat. No. 6,174,680 B1; Makrogiorgos, PCT Publication No. WO 00/39345.

In another example, the abasic site may be chemically modified, then the modified abasic site covalently or non-covalently attached to a suitable reactive group on a substrate. For example, the aldehyde (in the abasic site) can be oxidized or reduced (using methods known in the art), then covalently immobilized to a substrate using, e.g., reductive amination or various oxidative processes.

The substrate may consist of many materials, limited primarily by capacity to immobilize (or, in some embodiments, capacity for derivatization to immobilize) any of a number of chemically reactive groups and compatibility with the synthetic chemistry used to immobilize the polynucleotide comprising an abasic site. The substrate can be a solid or semi-solid support, which may be made, e.g., from glass, plastic (e.g., polystyrene, polypropylene, nylon), polyacrylamide, nitrocellulose, or other materials such as metals. As described herein, the substrate can be functionalized, if necessary to add a suitable reactive group (to which the abasic site is covalently or non-covalently immobilized). The polynucleotides may also be spotted as a matrix on substrates comprising paper, glass, plastic, polystyrene, polypropylene, nylon, polyacrylamide, nitrocellulose, silicon, optical fiber or any other suitable solid or semi-solid (e.g., thin layer of polyacrylamide gel, assuming that the substrate is suitably functionalized, as described herein (Khrapko, et al., DNA Sequence (1991), 1:375-388)).

An array may be assembled as a two-dimensional matrix on a planar substrate or may have a three-dimensional configuration comprising pins, rods, fibers, tapes, threads, beads, particles, microtiter wells, capillaries, cylinders and any other arrangement suitable for hybridization and detection of template molecules. In one embodiment the substrate to which the polynucleotide (or fragments thereof) is immobilized is magnetic beads or particles. In another embodiment, the solid substrate comprises an optical fiber. In yet another embodiment, the polynucleotides are dispersed in fluid phase within a capillary which, in turn, is immobilized with respect to a solid phase.

In another embodiment, the substrate comprises a polypeptide, a protein, a peptide, carbohydrates, cells, microorganisms and fragments and products thereof, an organic molecule, an inorganic molecule, carrier molecules, PEG, amino-dextran, carbohydrates, supramolecular assemblies, organelles, cells, microorganisms, organic molecules, inorganic molecules, or any substance for which immobilization sites for polynucleotides comprising abasic sites naturally exist, can be created (e.g. by functionalizing or otherwise modifying the substrate) or can be developed. In one embodiment, the substrate is a polynucleotide.

The substrate may be an analyte. Typical analytes may include, but are not limited to antibodies, proteins (including enzymes), peptides, nucleic acid molecules or segments thereof, carrier molecules, PEG, amino-dextran, carbohydrates, supramolecular assemblies, organelles, cells, microorganisms, organic molecules, inorganic molecules, or any substance for which immobilization sites for polynucleotides comprising abasic sites naturally exist, can be created (e.g. by functionalizing the analyte) or can be developed.

It is understood that a substrate may be a member(s) of a binding pair. Non-limiting examples of a binding pair include a protein:protein binding pair, and a protein:antibody binding pair. In another embodiment, polynucleotides (or fragments thereof) are immobilized to (tag) a molecular library of substrates, e.g., a molecular library of chemical compounds, a phage peptide display library, or a library of antibodies.

In some embodiments, the substrate (to which the polynucleotide is immobilized) is an enzyme, such that enhanced detection of hybridization of the polynucleotide is provided. For example, a polynucleotide immobilized to an enzyme can be hybridized to a microarray, and hybridized polynucleotide detected by contacting the microarray with a defined substrate.

In embodiments of the invention involving cleavage of the phosphodiester backbone at an abasic site (whereby fragments of the synthesized nucleic acid are generated), the cleaved fragments can also be immobilized to a substrate using any method known in the art for immobilization of a nucleic acid to a substrate. As used herein, "immobilization" includes both covalent attachment and non-covalent association. In one embodiment, a polynucleotide is immobilized to a substrate directly via the abasic site. In another embodiment, a polynucleotide is immobilized to a substrate directly or indirectly via an attached or associated label.

For example, single or double stranded polynucleotide fragments (generally single stranded) can be immobilized to a solid or semi-solid support or substrate, which may be made, e.g., from plastics, ceramics, metals, acrylamide, cellulose, nitrocellulose, glass, polystyrene, polyethylene vinyl acetate, polypropylene, polymethacrylate, polyethylene, polyethylene oxide, polysilicates, polycarbonates, Teflon®, fluorocarbons, nylon, silicon rubber, polyanhydrides, polyglycolic acid, polylactic acid, polyorthoesters, polypropylfumerate, collagen, glycosaminoglycans, and polyamino acids, and other materials. Substrates may be two-dimensional or three-dimensional in form, such as gels, membranes, thin films, glasses, plates, cylinders, beads, magnetic beads, optical fibers, woven fibers, microtiter well, capillaries, etc. For example, the fragments can be contacted with a solid or semi-solid substrate, such as a glass slide, which is coated with a reactive group which will form a covalent link with the reactive group that is on the polynucleotide fragment and become covalently immobilized to the substrate.

Microarrays comprising the nucleotide fragments can be fabricated using a Biodot (BioDot, Inc. Irvine, Calif.) spotting apparatus and aldehyde-coated glass slides (CEL Associates, Houston, Tex.). Polynucleotide fragments can be spotted onto the aldehyde-coated slides following suitable functionalization, and processed according to published procedures (Schena et al., Proc. Natl. Acad. Sci. U.S.A. (1995) 93:10614-10619), provided suitable care is taken to avoid interfering with other desired reactions at the abasic sites. Arrays can also be printed by robotics onto glass, nylon (Ramsay, G., Nature Biotechnol. (1998), 16:40-44), polypropylene (Matson, et al., Anal Biochem. (1995), 224(1):110-6), and silicone slides (Marshall, A. and Hodgson, J., Nature Biotechnol. (1998), 16:27-31). Other approaches to array assembly include fine micropipetting within electric fields (Marshall and Hodgson, supra), and spotting the polynucleotides directly onto positively coated plates. Methods such as those using amino propyl silane surface chemistry are also known in the art, as disclosed at www.cmt.corning.com and cmgm.stanford.edu/pbrown/.

One method for making microarrays is by making high-density polynucleotide arrays. Techniques are known for rapid deposition of polynucleotides (Blanchard et al., Biosensors & Bioelectronics, 11:687-690). In principle, and as noted above, any type of array, for example, dot blots on a nylon hybridization membrane, could be used. However, as will be recognized by those skilled in the art, very small arrays will frequently be preferred because hybridization volumes will be smaller. Very small arrays may include a high or low density of probes.

Methods for immobilizing polynucleotide fragments to analytes (as described herein) are known in the art. See, e.g., U.S. Pat. Nos. 6,309,843; 6,306,365; 6,280,935; and 6,087,103 (and methods discussed therein).

Applications Using the Labeling and/or Fragmentation and/or Immobilization Methods of the Invention The methods and compositions of the invention can be used for a variety of purposes. For purposes of illustration, methods of producing a hybridization probe or target, characterizing and/or quantitating nucleic acid, detecting a mutation, preparing a subtractive hybridization probe, detection (using the hybridization probe), and determining a gene expression profile, using the labeled and/or fragmented nucleic acids generated by the methods of the invention, are described.

Immobilized polynucleotides, for example on a microarray, prepared according to any of the methods of the invention, are also useful for methods of analyzing and characterizing nucleic acids, including methods of hybridizing nucleic acids, methods of characterizing and/or quantitating nucleic acids, methods of detecting a mutation in a nucleic acids, and methods of determining a gene expression profile, as described below, and these applications likewise apply to immobilized polynucleotides.

A. Method of Producing a Hybridization Probe or Target

The polynucleotides obtained by the methods of the invention are useful as hybridization probes or targets. As used herein, "probe" refers to a reference polynucleotide or oligonucleotide, for example immobilized to a substrate or in solution, and "target" refers to a polynucleotide or oligonucleotide from a sample to be analyzed by hybridization to the probe. In some embodiments, the target is detectably labeled. In other embodiments, a hybridization target generated by a method of the invention is unlabeled and its interaction with a probe is detected indirectly. Accordingly, in one aspect, the invention provides methods for generating hybridization targets, comprising generating labeled polynucleotides using any of the methods described herein, and using the labeled polynucleotides as a hybridization target. In another embodiment, the invention provides methods for generating a hybridization target, comprising generating labeled polynucleotide fragments using any of the methods described herein, and using the labeled polynucleotide fragments as a hybridization target. The labeled polynucleotide (or polynucleotide fragments) can be produced from any template, including RNA, DNA, genomic DNA (including global genomic DNA amplification), and libraries (including cDNA, genomic or subtractive hybridization library). The invention also provides methods of hybridizing using the hybridization targets to a probe as described herein. In another aspect, the invention provides methods for generating hybridization probes, comprising generating polynucleotides or polynucleotide fragments using any of the methods described herein. In one embodiment, a probe comprising a polynucleotide or polynucleotide fragment generated by a method of the invention is immobilized to a solid support. In one embodiment, the probe is labeled and is immobilized to a support via the label (for example, indirect immobilization via a member of a specific binding pair). In another embodiment, the probe is unlabeled.

B. Characterization of Nucleic Acids

The labeled and/or fragmented nucleic acids obtained by the methods of the invention are amenable to further characterization.

The labeled and/or fragmented nucleic acids (i.e., products of any of the methods described herein), can be analyzed using, for example, probe hybridization techniques known in the art, such as Southern and Northern blotting, and hybridizing to probe arrays. They can also be analyzed by electrophoresis-based methods, such as differential display and size characterization, which are known in the art.

In one embodiment, the methods of the invention are utilized to generate labeled and/or fragmented nucleic acids, and analyze the labeled and/or fragmented nucleic acids by contact with a probe. The labeled and/or fragmented nucleic acid can be produced from any template known in the art, including RNA, DNA, genomic DNA (including global genomic DNA amplification), and libraries (including cDNA, genomic or subtractive hybridization library).

In one embodiment, the methods of the invention are utilized to generate labeled and/or fragmented nucleic acids which are analyzed (for example, detection and/or quantification) by contacting them with, for example, microarrays (of any suitable substrate, which includes glass, chips, plastic), beads, or particles, that comprise suitable probes such as cDNA and/or oligonucleotide probes. Thus, the invention provides methods to characterize (for example, detect and/or quantify and/or identify) a labeled and/or fragmented nucleic acid by analyzing the labeled products, for example, by hybridization of the labeled products to, for example, probes immobilized at, for example, specific locations on a solid or semi-solid substrate, probes immobilized on defined particles (including beads, such as Bead Array, Illumina), or probes immobilized on blots (such as a membrane), for example arrays, or arrays of arrays. Immobilized probes include immobilized probes generated by the methods described herein, and also include at least the following: cDNA and synthetic oligonucleotides, which can be synthesized directly on the substrate.

Other methods of analyzing labeled products are known in the art, such as, for example, by contacting them with a solution comprising probes, followed by extraction of complexes comprising the labeled products and probes from solution. The identity of the probes provides characterization of the sequence identity of the products, and thus by extrapolation can also provide characterization of the identity of a template from which the products were prepared (for example, the identity of an RNA in a solution). For example, hybridization of the labeled products is detectable, and the amount of specific labels that are detected is proportional to the amount of the labeled products prepared from a specific RNA sequence of interest. This measurement is useful for, for example, measuring the relative amounts of the various RNA species in a sample, which are related to the relative levels of gene expression, as described herein. The amount of labeled products (as indicated by, for example, detectable signal associated with the label) hybridized at defined locations on an array can be indicative of the detection and/or quantification of the corresponding template RNA species in the sample.

Methods of characterization include sequencing by hybridization (see, e.g., Dramanac, U.S. Pat. No. 6,270,961) and global genomic hybridization (also termed comparative genome hybridization) (see, e.g., Pinkel, U.S. Pat. No. 6,159,685).

In another aspect, the invention provides a method of quantitating labeled and/or fragmented nucleic acids comprising use of an oligonucleotide (probe) of defined sequence (which may be immobilized, for example, on a microarray).

C. Mutation Detection Utilizing the Methods of the Invention

The labeled and/or fragmented nucleic acids generated according to the methods of the invention are also suitable for analysis for the detection of any alteration in the template nucleic acid sequence (from which the labeled and/or fragmented nucleic acids are synthesized), as compared to a reference nucleic acid sequence which is identical to the template nucleic acid sequence other than the sequence alteration. The sequence alterations may be sequence alterations present in the genomic sequence or may be sequence alterations which are not reflected in the genomic DNA sequences, for example, alterations due to post transcriptional alterations, and/or mRNA processing, including splice variants. Sequence alterations (interchangeably called "mutations") include deletion, substitution, insertion and/or transversion of one or more nucleotide.

Accordingly, the invention provides methods of detecting presence or absence of a mutation in a template, comprising: (a) generating a labeled polynucleotide, or fragments thereof, by any of the methods described herein; and (b) analyzing the labeled polynucleotide, or fragments thereof, whereby presence or absence of a mutation is detected. In some embodiments, the labeled polynucleotide, or fragments thereof, is compared to a labeled reference template, or fragments thereof. Step (b) of analyzing the labeled polynucleotide, or fragments thereof, whereby presence or absence of a mutation is detected, can be performed by any method known in the art. In some embodiments, probes for detecting mutations are provided as a microarray.

Any alteration in the test nucleic acid sequence, such as base substitution, insertions or deletion, could be detected using this method. The method is expected to be useful for detection of specific single base polymorphism, SNP, and the discovery of new SNPs.

Other art recognized methods of analysis for the detection of any alteration in the template nucleic acid sequence, as compared to a reference nucleic acid sequence, are suitable for use in the methods of the present invention. For example, essentially any hybridization-based method of detection of mutations is suitable for use with the labeled and/or fragmented nucleic acids produced by the methods of the invention.

D. Methods of Preparing a Subtractive Hybridization Probe

The labeled and/or fragmented nucleic acids methods of the invention are particularly suitable for use in preparation of labeled and/or fragmented subtractive hybridization probes. For example, two nucleic acid populations, one sense and one antisense, can be allowed to mix together with one population present in molar excess ("driver"). Sequence present in both populations will form hybrids, while sequences present in only one population remain single-stranded. Thereafter, various well-known techniques are used to separate the unhybridized molecules representing differentially expressed sequences. See, e.g., Hamson et al., U.S. Pat. No. 5,589,339; Van Gelder, U.S. Pat. No. 6,291,170. Labeled and/or fragmented subtractive hybridization probe is then labeled and/or fragmented according to the methods of the invention described herein.

E. Comparative Hybridization

In another aspect, the invention provides methods for comparative hybridization (such as comparative genomic hybridization), said method comprising: (a) preparing a first population of labeled polynucleotides or fragments thereof from a first template polynucleotide sample using any of the methods described herein; (b) comparing hybridization of the first population to at least one probe with hybridization of a second population of labeled polynucleotides or fragments thereof. In some embodiments, the at least one probe is a chromosomal spread. In still other embodiments, the at least one probe is provided as a microarray. In other embodiments, the second population of labeled polynucleotides, or fragments thereof, are prepared from a second polynucleotide sample using any of the methods described herein. In some embodiments, the first population and second population comprise detectably different labels. In some embodiments, step (b) of comparing comprises determining amount of said products, whereby the amount of the first and second polynucleotide templates is quantified.

In some embodiments, comparative hybridization comprises preparing a first population of labeled polynucleotides (which can be polynucleotide fragments) according to any of the methods described herein, wherein the template from which the first population is synthesized is genomic DNA. A second population of labeled polynucleotides (to which the first population is desired to be compared) is prepared from a second genomic DNA template. The first and second populations are labeled with different labels. The hybridized first and second populations are mixed, and hybridized to an array or chromosomal spread. The different labels are detected and compared.

Reaction Conditions and Detection

Appropriate reaction media and conditions for carrying out the methods of the invention are those that permit nucleic acid synthesis according to the methods of the invention. Such media and conditions are known to persons of skill in the art, and are described in various publications, such as U.S. Pat. Nos. 6,190,865; 5,554,516; 5,716,785; 5,130,238; 5,194,370; 6,090,591; 5,409,818; 5,554,517; 5,169,766; 5,480,784; 5,399,491; 5,679,512; PCT Publication No. WO 99/42618; Mol. Cell Probes (1992) 251-6; and Anal. Biochem. (1993) 211:164-9. For example, a buffer may be Tris buffer, although other buffers can also be used as long as the buffer components are non-inhibitory to enzyme components of the methods of the invention. The pH is from about 5 to about 11, more preferably from about 6 to about 10, from about 7 to about 9, and from about 7.5 to about 8.5. The reaction medium can also include bivalent metal ions such as $Mg^{2+}$ or $Mn^{2+}$, at a final concentration of free ions that is within the range of from about 0.01 to about 15 mM, and most preferably from about 1 to 10 mM. The reaction medium can also include other salts, such as KCl or NaCl, that contribute to the total ionic strength of the medium. For example, the range of a salt such as KCl is preferably from about 0 to about 125 mM, more preferably from about 0 to about 100 mM, and most preferably from about 0 to about 75 mM. The reaction medium can further include additives that could affect performance of the amplification reactions, but that are not integral to the activity of the enzyme components of the methods. Such additives include proteins such as BSA, single strand binding proteins (e.g., T4 gene 32 protein), and non-ionic detergents such as NP40 or Triton. Reagents, such as DTT, that are capable of maintaining enzyme activities can also be included. Such reagents are known in the art. Where appropriate, an RNase inhibitor (such as Rnasin) that does not inhibit the activity of the RNase employed in the method (if any) can also be included. Any aspect of the methods of the invention can occur at the same or varying temperatures. The synthesis reactions (particularly, primer extension other than the first and second strand cDNA synthesis steps, and strand displacement) can be performed isothermally, which avoids the cumbersome thermocycling process. The synthesis reaction is carried out at a temperature that permits hybridization of oligonucleotides (primer) to the template polynucleotide and primer extension products, and that does not substantially inhibit the activity of the enzymes employed. The temperature can be in the range of preferably about 25° C. to about 85° C., more preferably about 30° C. to about 80° C., and most preferably about 37° C. to about 75° C. In some embodiments that include RNA transcription, the temperature for the transcription steps is lower than the temperature(s) for the preceding steps. In these embodiments, the temperature of the transcription steps can be in the range of preferably about 25° C. to about 85° C., more preferably about 30° C. to about 75° C., and most preferably about 37° C. to about 70° C.

Nucleotides that can be employed for synthesis of the nucleic acids in the methods of the invention are provided in the amount of from about 50 to about 2500 µM, about 100 to about 2000 µM, about 200 to about 1700 µM, and about 250 to about 1500 µM. The oligonucleotide components of the synthesis reactions of the invention are generally in excess of the number of template nucleic acid sequence to be replicated. They can be provided at about or at least about any of the following: 10, $10^2$, $10^4$, $10^6$, $10^8$, $10^{10}$, $10^{12}$ times the amount of target nucleic acid. Composite primers can be provided at about or at least about any of the following concentrations: 50 nM, 100 nM, 500 nM, 1000 nM, 2500 nM, 5000 nM.

Optionally, the polynucleotide template (i.e., polynucleotide comprising a canonical nucleotide, or polynucleotide comprising a methylated nucleotide) can be treated with hydroxylamine (or any other suitable agent) to remove any aldehydes that may have formed spontaneously in the nucleic acid. See, e.g., Makrogiorgos, PCT Publication No. WO 00/39345.

For convenience, the cleavage of a base portion of that polynucleotide by an enzyme capable of cleaving a base portion of the canonical nucleotide (or capable of cleaving a base portion of the methylated nucleotide, in embodiments involving methylation), and the cleavage of the phosphodiester backbone at the abasic site, are described as separate steps. It is understood that these steps may be performed simultaneously.

Appropriate reaction media and conditions for carrying out the cleavage of a base portion of a canonical nucleotide according to the methods of the invention are those that permit cleavage of a base portion of a canonical nucleotide. Such media and conditions are known to persons of skill in the art, and are described in various publications, such as Sohail et al, NAR 2003, 31: 2990-94; A. Sartori et al, JBC 2001, 276: 29979-29986; U.S. Pat. No. 6,017,704. In some embodiments involving cleavage of a canonical nucleotide, dUTP is generated as an intermediate and cleavage of a base portion of dUTP is necessary to generate the abasic site. Methods for cleaving a base portion of dUTP are known in the art. See, e.g., Lindahl, *PNAS* (1974) 71(9):3649-3653; Jendrisak, U.S. Pat. No. 6,190,865 B1; U.S. Pat. No. 5,035,996; U.S. Pat. No. 5,418,149.

Appropriate reaction media and conditions for carrying out the cleavage of a base portion of a methylated nucleotide according to the methods of the invention are those that permit cleavage of a base portion of a methylated nucleotide. Such media and conditions are known to persons of skill in the art, and are described in various publications, such as Wolffe et al., Proc. Nat. Acad. Sci. USA 96:5894-5896, 1999); Zhu et al., Proc. Natl. Acad. Sci. USA 98:5031-6, 2001; Zhu et al., Nuc. Acid Res. 28:4157-4165, 2000; Neddermann et al., J. B. C. 271:12767-74, 1996; Vairapandi & Duker, Oncogene 13:933-938, 1996; Vairapandi et al., J. Cell. Biochem. 79:249-260, 2000.

In embodiments involving cleavage of the phosphodiester backbone, appropriate reaction media and conditions for carrying out the cleavage of the phosphodiester backbone at an abasic site according to the methods of the invention are those that permit cleavage of the phosphodiester backbone at an abasic site. Such media and conditions are known to persons of skill in the art, and are described in various publications, such as Bioorgan. Med. Chem (1991) 7:2351; Sugiyama, Chem. Res. Toxicol. (1994) 7: 673-83; Horn, Nucl. Acids. Res., (1988) 16:11559-71); Lindahl, PNAS (1974) 71(9): 3649-3653; Jendrisak, U.S. Pat. No. 6,190,865 B1; Shida, Nucleic Acids Res. (1996) 24(22):4572-76; Srivastava, J. Biol Chem. (1998) 273(13):21203-209; Carey, Biochem. (1999) 38:16553-60; Chem Res Toxicol (1994) 7:673-683. For example, *E. coli* AP endonuclease IV is added to reaction conditions as described above. AP Endonuclease IV can be added at the same or different time as the agent (such as an enzyme) capable of cleaving the base portion of a canonical nucleotide.

In another example, nucleic acids containing abasic sites are heated in a buffer solution containing an amine, for example, 25 mM Tris-HCl and 1-5 mM magnesium ions, for 10-30 minutes at 70° C. to 95° C. Alternatively, 1.0 M piperidine (a base) is added to polynucleotide comprising an abasic site which has been precipitated with ethanol and vacuum dried. The solution is then heated for 30 minutes at 90° C. and lyophilized to remove the piperidine. In another example, cleavage is affected by treatment with basic solution, e.g., 0.2 M sodium hydroxide at 37° for 15 minutes. See Nakamura (1998) Cancer Res. 58:222-225. In yet another example, incubation at 37° C. with 100 mM N,N'-dimethylethylenediamine acetate, pH 7.4 is used to cleave. See McHugh and Knowland, (1995) Nucl. Acids Res. 23 (10) 1664-1670; see also co-pending co-owned U.S. patent application Ser. No. 10/441,663.

In one embodiment, the reaction conditions are the same for the cleavage of a base portion of the canonical nucleotide (or in embodiments, involving methylation analysis, cleavage of a base portion of the methylated nucleotide) and for the cleavage of the phosphodiester backbone at abasic sites. In another embodiment, different reaction conditions are used for these reactions.

In embodiments involving labeling at an abasic site, appropriate reaction media and conditions for carrying out the labeling at an abasic site according to the methods of the invention are those that permit labeling at an abasic site. Such reaction mixtures and conditions are known to persons of skill in the art, and are described in various publications, such as co-pending co-owned U.S. patent application Ser. No. 10/441,663; Makrigiorgos, PCT Publication No. WO 00/39345; Srivastava, *J. Biol. Chem*. (1998) 273(33): 21203-209; Makrigiorgos, Int J. Radiat. Biol. (1998) 74(1):99-109; Makrigiorgos, U.S. Pat. No. 6,174,680 B1; Makrigiorgos, PCT Publication No. WO 00/39345; Boturyn (1999) Chem. Res. Toxicol. 12:476-482. See, also, Adamczyk (1998)

Bioorg. Med. Chem. Lett. 8(24):3599-3602; Adamczyk (1999) Org. Lett. 1(5):779-781; Kow (2000) Methods 22(2): 164-169; Molecular Probes Handbook, Section 3.2 (www.probes.com); Horn (Nucl. Acids. Res., (1988) 16:11559-71). For example, 5-(((2-(carbohydrazino)-methyl)thio)acetyl) aminofluorescein, aminooxyacetyl hydrazide (FARP); N-(aminooxyacetyl)-N'-(D-biotinoyl)hydrazine, trifluoroacetic acid salt (ARP); Alexa Fluor 555 (Molecular Probes); aminooxy-derivatized Alexa Fluor 555; and other aldehyde-reactive reagents can be reacted with a polynucleotide comprising abasic sites. The buffer can be sodium citrate or sodium phosphate buffer, though other buffers are acceptable as long as the buffer components are non-inhibitory to enzyme components and/or desired chemical reactions used in the methods of the invention. The pH is preferably from about 3 to about 11, more preferably from about 4 to about 10, even more preferably from about 4 to about 8, and most preferably from about 4 to about 7. The reaction can be conducted at room temperature to 85° C. (in some embodiments, at about 55° C.), though other temperatures are suitable as long as the temperature is non-inhibitory to enzyme components and/or desired chemical reactions used in the methods of the invention. Generally, the label (e.g. ARP or FARP) is added at about 1-10 mM, in some embodiments at 2-5 mM, though other concentrations are suitable. If an antibody label is used, conditions for antibody binding are well-known in the art, and can be as described herein. Optionally, a stop buffer can be used that neutralizes the pH of the labeling reaction, thereby stopping the labeling reaction and optionally, facilitating subsequent purification of labeled product.

In embodiments involving immobilization of a polynucleotide at an abasic site, appropriate reaction media and conditions for carrying out the immobilization at an abasic site according to the methods of the invention are those that permit immobilization at an abasic site. Such reaction mixtures and conditions are known to persons of skill in the art, and are described in various publications, such as Luktanov, U.S. Pat. No. 6,339,147; Van Ness, U.S. Pat. No. 5,667,976; Bangs Laboratories, Inc. TechNote 205 (available at bangslabs.com); Ghosh, Anal. Biochem (1989) 178:43-51; O'Shannessy, Anal. Biochem. (1990) 191:1-8; Wilchek, Methods Enzymol. (1987) 138:429-442; Baumgartner, Anal. Biochem. (1989) 181:182-189; Zalipsky, Bioconjugate Chem. (1995) 6: 150-165, and references cited therein. In some cases, the initial product can be stabilized by reduction with sodium cyanoborohydride or similar agents known in the art. See, e.g., O'Shannessy, supra.

In one embodiment, the foregoing components are added simultaneously at the fragmentation and/or labeling and/or immobilization processes. In another embodiment, components are added in any order prior to or after appropriate timepoints during the synthesis step. Such timepoints, some of which are noted below, can be readily identified by a person of skill in the art. In these embodiments, the reaction conditions and components may be varied between the different reactions.

The fragmenting and/or labeling and/or immobilization process can be stopped at various timepoints, and resumed at a later time. Said timepoints can be readily identified by a person of skill in the art. Methods for stopping the reactions are known in the art, including, for example, cooling the reaction mixture to a temperature that inhibits enzyme activity or heating the reaction mixture to a temperature that destroys an enzyme. Methods for resuming the reactions are also known in the art, including, for example, raising the temperature of the reaction mixture to a temperature that permits enzyme activity or replenishing a destroyed (depleted) enzyme or other reagent. In some embodiments, one or more of the components of the reactions is replenished prior to, at, or following the resumption of the reactions. Alternatively, the reaction can be allowed to proceed (i.e., from start to finish) without interruption.

The reaction can be allowed to proceed without purification of intermediate complexes, for example, to remove primer. Products can be purified at various timepoints, which can be readily identified by a person of skill in the art.

Compositions and Kits of the Invention

The invention also provides compositions and kits used in the methods described herein. The compositions may be any component(s), reaction mixture and/or intermediate described herein, as well as any combination. For example, the invention provides a composition comprising an agent (such as an enzyme) capable of cleaving a base portion of a canonical nucleotide, optionally an agent (such as an enzyme) capable of effecting cleavage of a phosphodiester backbone at an abasic site, and an agent capable of labeling an abasic site. In some embodiments, the invention provides compositions further comprising a composite primer, said composite comprising a DNA portion and a 5' RNA portion. In still other embodiments, the 5' RNA portion of the composite primer is adjacent to the 3' DNA portion, the RNA portion of the composite primer consists of about 10 to about 20 nucleotides and the DNA portion of the composite primer consists of about 7 to about 20 nucleotides. In still other embodiments, the composition comprises a second, different composite primer. In some embodiments, the RNA portion of the composite primer comprises the following ribonucleotide sequence: 5'-GACGGAUGCGGUCU-3' (SEQ ID NO: 1). In still other embodiments, the compositions further comprise one or more of (a) a mixture of dATP, dTTP, dCTP, and dGTP; (b) a DNA polymerase; and (c) RNAse H. In still other embodiments, the compositions further comprise one or more of (a) MgCl2 solution; (b) acetic acid solution; and optionally, (c) a stop buffer comprising 1.5M Tris, pH 8.5. In some embodiments, the agent capable of cleaving the phosphodiester backbone at an abasic site is an amine (such as N,N'-dimethylethylenediamine); and/or E. coli Endonuclease IV. In some embodiments, the agent capable of labeling an abasic site is ARP, FARP, Alexa Fluor 555 hydrazide (Order No. A-20501, Molecule Probes, Eugene Oreg.), and/or an aminooxy-modified Alexa Fluor 555 (see copending co-owned U.S. patent application Ser. No. 10/441,663).

In another example, the invention provides a composition comprising an agent (such as an enzyme) capable of cleaving a base portion of a methylated nucleotide, optionally, an agent (such as an enzyme) capable of effecting cleavage of a phosphodiester backbone at an abasic site, and an agent capable of labeling an abasic site. In some embodiments, the agent capable of cleaving a base portion of a methylated nucleotide is 5-methylcytosine DNA glycosylase (5-MCDG), or 3-methyladenosine-DNA glycosylase. In some embodiments, the agent capable of cleaving the phosphodiester backbone at an abasic site is an amine (such as N,N'-dimethylethylenediamine); and/or E. coli Endonuclease IV. In some embodiments, the agent capable of labeling an abasic site is ARP, FARP, Alexa Fluor 555 hydrazide (Order No. A-20501, Molecule Probes, Eugene Oreg.), and/or an aminooxy-modified Alexa Fluor 555 (see copending co-owned U.S. patent application Ser. No. 10/441,663).

The compositions are generally in lyophilized or aqueous form (if appropriate), preferably in a suitable buffer.

The invention also provides compositions comprising the labeled and/or fragmented products described herein.

Accordingly, the invention provides a population of labeled and/or fragmented polynucleotides, which are produced by any of the methods described herein (or compositions comprising the products).

The invention also provides compositions comprising the immobilized polynucleotides or immobilized polynucleotide fragments described herein. In some embodiments, the immobilized polynucleotide (or immobilized fragment, in embodiments involving fragmentation) is labeled, as described herein. Accordingly, the invention provides a population of immobilized polynucleotides or immobilized polynucleotide fragments which are produced by any of the methods described herein (or compositions comprising the products).

The invention also provides reaction mixtures (or compositions comprising reaction mixtures) which contain various combinations of components described herein. Examples of reaction mixtures have been described.

The invention provides kits for carrying out the methods of the invention. Accordingly, a variety of kits are provided in suitable packaging. The kits may be used for any one or more of the uses described herein The kits of the invention comprise one or more containers comprising any combination of the components described herein, and the following are examples of such kits.

In some embodiments, the invention provides kits comprising an agent (such as an enzyme) capable of cleaving a base portion of a canonical nucleotide, optionally an agent (such as an enzyme) capable of effecting cleavage of a phosphodiester backbone at an abasic site, and an agent capable of labeling an abasic site. In some embodiments, the invention provides kits further comprising a composite primer, said composite comprising a DNA portion and a 5' RNA portion. In still other embodiments, the 5' RNA portion of the composite primer is adjacent to the 3' DNA portion, the RNA portion of the composite primer consists of about 10 to about 20 nucleotides and the DNA portion of the composite primer consists of about 7 to about 20 nucleotides. In still other embodiments, the kits comprise a second, different composite primer. In some embodiments, the RNA portion of the composite primer comprises the following ribonucleotide sequence: 5'-GACGGAUGCGGUCU-3' (SEQ ID NO: 1). In still other embodiments, the kits further comprise one or more of (a) a mixture of dATP, dTTP, dCTP, and dGTP; (b) a DNA polymerase; and (c) RNAse H. In still other embodiments, the kits further comprise one or more of (a) MgCl2 solution; (b) acetic acid solution; and optionally, (c) a stop buffer comprising 1.5M Tris, pH 8.5. In some embodiments, the invention provides a kit comprising RNAseH, and an agent (such as an enzyme) capable of cleaving a base portion of a canonical nucleotide. RNase H. In some embodiments, the invention provides a kit comprising a composite primer comprising an RNA portion and a 3' DNA portion and instructions for any of the methods for labeling and/or fragmenting a polynucleotide comprising a canonical nucleotide described herein. In some embodiments, the agent capable of cleaving the phosphodiester backbone at an abasic site is an amine (such as N,N'-dimethylethylenediamine); and/or E. coli Endonuclease IV. In some embodiments, the agent capable of labeling an abasic site is ARP, FARP, Alexa Fluor 555 hydrazide (Order No. A-20501, Molecule Probes, Eugene Oreg.), and/or an aminooxy-modified Alexa Fluor 555 (see copending co-owned U.S. patent application Ser. No. 10/441,663).

In another example, the invention provides kits comprising an agent (such as an enzyme) capable of cleaving a base portion of a methylated nucleotide, optionally, an agent (such as an enzyme) capable of effecting cleavage of a phosphodiester backbone at an abasic site, and an agent capable of labeling an abasic site. In some embodiments, the agent capable of cleaving a base portion of a methylated nucleotide is 5-methylcytosine DNA glycosylase (5-MCDG), or 3-methyladenosine-DNA glycosylase. In some embodiments, the agent capable of cleaving the phosphodiester backbone at an abasic site is an amine (such as N,N'-dimethylethylenediamine); and/or E. coli Endonuclease IV. In some embodiments, the agent capable of labeling an abasic site is ARP, FARP, Alexa Fluor 555 hydrazide (Order No. A-20501, Molecule Probes, Eugene Oreg.), and/or an aminooxy-modified Alexa Fluor 555 (see copending co-owned U.S. patent application Ser. No. 10/441,663).

Kits may also include one or more suitable buffers (as described herein). One or more reagents in the kit can be provided as a dry powder, usually lyophilized, including excipients, which on dissolution will provide for a reagent solution having the appropriate concentrations for performing any of the methods described herein. Each component can be packaged in separate containers or some components can be combined in one container where cross-reactivity and shelf life permit.

The kits of the invention may optionally include a set of instructions, generally written instructions, although electronic storage media (e.g., magnetic diskette or optical disk) containing instructions are also acceptable, relating to the use of components of the methods of the invention for the intended methods of the invention, and/or, as appropriate, for using the products for purposes such as, for example preparing a hybridization probe or target, expression profiling, preparing a microarray, or characterizing a nucleic acid. The instructions included with the kit generally include information as to reagents (whether included or not in the kit) necessary for practicing the methods of the invention, instructions on how to use the kit, and/or appropriate reaction conditions.

The component(s) of the kit may be packaged in any convenient, appropriate packaging. The components may be packaged separately, or in one or multiple combinations.

The relative amounts of the various components in the kits can be varied widely to provide for concentrations of the reagents that substantially optimize the reactions that need to occur to practice the methods disclosed herein and/or to further optimize the sensitivity of any assay.

The following examples are provided to illustrate, but not to limit, the invention.

EXAMPLES

Example 1

Acid-Catalyzed Fragmentation and Labeling of cDNA

Single stranded cDNA was prepared from universal human total RNA (Stratagene, La Jolla Calif.). Pooled purified cDNA product at a concentration of 145 µg/mL in water was aliquoted into each of five 200 µL PCR tubes, dispensing 13 µL or 1.89 µg into each tube. 12 µL water was then added to each tube, followed by 2.5 µL of 0.5 M glycolic acid buffer (prepared by dissolving glycolic acid in water at a concentration of 1.0 M, adjusting pH with 1 M NaOH, then diluting to 0.5 M with water). Three tubes received buffer at a pH of 3.0, and two received buffer of pH 3.5. The pH 3 tubes were heated at 95° C. for 5 minutes and 65° for 5 minutes or 30 minutes. The pH 3.5 tubes were heated at 65° C. for 5 minutes or 30 minutes, all in a MJ Research Peltier Effect thermal cycler. Tubes were then held briefly on ice for the next step.

To each tube was added 5 µL of 0.5 M acetate buffer pH 4.33 (prepared by pH adjustment of acetic acid with NaOH), followed by 1 µL of 1 M NaOH in each pH 3.0 tube and 0.7 µL of 1 M NaOH in pH 3.5 tubes. All tubes then received 2 µL of 0.2 M $MgCl_2$ and 2.7 µL of a biotinylating reagent. This reagent contained 11.7 mg/mL of ARP (N-(aminooxyacetyl)-N'-(D-biotinoyl) hydrazine, trifluoroacetic acid salt) (Molecular Probes, Eugene, Oreg.) dissolved in a 22.5 mM solution of dibasic sodium phosphate. All tubes were then incubated at 50° C. for 30 minutes, then 10 µL of 1 M Tris, pH 8.5 was added to each tube.

The contents of each tube were purified using a single CentriSep size exclusion column (Princeton Separations, Adelphia, N.J.) following the manufacturer's instructions.

Concentration of recovered product was estimated from $A_{260}$ assuming that 33 µg/mL of DNA gives $A_{260}$=1.0. It was noted that the $A_{260}/A_{280}$ ratio for the product heated at 95° C. was 1.75, while all other products gave ratios>1.9. Recoveries were 60-69%.

Extent of fragmentation and labeling was determined using a gel shift assay. Two aliquots of product, each containing 50 ng DNA (3.1-3.5 µL), were mixed in PCR tubes with 0.5 µL of 10× TE buffer (0.1 M Tris, 10 mM EDTA, pH 7.5). To one aliquot was added 3 µL of a 2.5 mg/mL solution of streptavidin (Sigma-Aldrich, St. Louis, Mo.) in water. After about 3 minutes incubation, 3 µL of 30% glycerol/bromophenol blue was added to each tube, and products were loaded and run on Novex 4-20% TBE gels (Invitrogen, Carlsbad, Calif.) following manufacturer's instructions. Bands were visualized by staining with Sybr Green II (Molecular Probes, Eugene, Oreg.) diluted 1:5,000 in gel buffer for 6 minutes, followed by imaging with an AlphaImager. Unreacted cDNA product and molecular weight markers were included as controls.

An image of the gel is shown in FIG. 1. Lane 1 is molecular weight markers, lane 2 is unreacted starting material, and subsequent lanes are paired products without or with streptavidin treatment. Lane 3 (5 min at 95° C., pH 3.0) shows extensive fragmentation of product compared to control in Lane 2. Average apparent size appears to be reduced to 400-500 bases, and the high molecular weight material in Lane 2 is virtually absent. Lane 4 shows that nearly all of the fragmented DNA is retarded by streptavidin, appearing as a high molecular weight smear, much of which does not enter the gel. The other extreme was represented by lanes 11 and 12 (5 min at 65° C., pH 3.5), where the length without streptavidin appeared identical to control, and some but not all of the product was shifted to higher molecular weight by streptavidin. The other pairs of lanes represented intermediate conditions in which little fragmentation was evident, but various extents of labeling were seen, as measured by streptavidin shift. Compared to lanes 11 and 12, longer time (30 min in Lanes 9 and 10), lower pH (pH 3.0 in Lanes 5 and 6), or both lower pH and longer time (30 min at pH 3.0 in Lanes 7 and 8) resulted in increased labeling.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entireties for all purposes.

We claim:

1. A method for fragmenting a polynucleotide comprising a methylated nucleotide and an unmethylated nucleotide, said method comprising:
    (a) mixing the polynucleotide with a methyl binding protein thereby forming a complex comprising the polynucleotide and the methyl binding protein;
    (b) cleaving a base portion of the unmethylated nucleotide of the polynucleotide in the complex with an agent capable of cleaving a base portion of an unmethylated nucleotide, whereby an abasic site is generated in the polynucleotide of the complex and wherein the methyl binding protein binds to the methylated nucleotide of the polynucleotide in the complex so that the agent is not capable of cleaving a base portion of the methylated nucleotide of the polynucleotide in the complex; and
    (c) fragmenting the phosphodiester backbone of the polynucleotide of the complex at the abasic site, whereby polynucleotide fragments are generated, wherein said fragmenting the phosphodiester backbone is performed with an amine, wherein the amine is N,N'-dimethylethylenediamine.

2. The method of claim 1, wherein the agent capable of cleaving a base portion of an unmethylated nucleotide comprises an enzyme.

3. The method of claim 2, wherein the unmethylated nucleotide is cytosine and the agent comprises cytosine deaminase in conjunction with uracil DNA glycosylase.

4. The method of claim 1, wherein the steps of the method are carried out simultaneously in the same reaction mixture.

5. The method of claim 1, further comprising contacting the polynucleotide with a polynucleotide binding protein.

6. The method of claim 5, wherein the polynucleotide binding protein is a DNA binding protein.

7. The method of claim 6, wherein the DNA binding protein is a transcription factor or a regulatory protein.

8. The method of claim 1, wherein the polynucleotide has a native methylation status, and the fragments generated are related to the native methylation status of the polynucleotide.

9. The method of claim 8, wherein the polynucleotide is hypermethylated, and further comprising a step of isolating the hypermethylated sequences of the polynucleotide.

10. The method of claim 1, further comprising labeling the abasic site, whereby the polynucleotide fragments are labeled.

11. The method of claim 10, wherein the labeled polynucleotide fragments comprise a detectable label.

12. The method of claim 11, further comprising hybridizing the labeled polynucleotide fragments to a probe.

13. The method of claim 12 wherein the probe is attached or hybridized to a solid support.

14. The method of claim 13, wherein the solid support is a microarray, or a bead array, or the probe is hybridized to a second probe attached to the solid support.

15. The method of claim 10, wherein the steps of the method are carried out simultaneously in the same reaction mixture.

16. The method of claim 10 wherein the agent capable of cleaving a base portion of an unmethylated nucleotide comprises an enzyme.

17. The method of claim 16, wherein the unmethylated nucleotide is cytosine and the agent comprises cytosine deaminase in conjunction with uracil DNA glycosylase.

18. A method of capturing a methylated portion of a polynucleotide that comprises a methylated nucleotide and an unmethylated nucleotide, the method comprising:
  (a) treating the polynucleotide with a methyl binding protein thereby forming a complex comprising the polynucleotide and the methyl binding protein, wherein the methyl binding protein binds to the methylated nucleotide of the polynucleotide in the complex;
  (b) cleaving a base portion of an unmethylated nucleotide with an agent capable of cleaving a base portion of an unmethylated nucleotide in a portion of the polynucleotide not bound to the methyl binding agent, whereby an abasic site in the polynucleotide of the complex is generated;
  (c) fragmenting the phosphodiester backbone at the abasic site of the polynucleotide, whereby polynucleotide fragments are generated, wherein said fragmenting the phosphodiester backbone is performed with an amine, wherein the amine is N,N'dimethylethylenediamine; and
  (d) capturing polynucleotide fragments comprising the methylated nucleotide from the polynucleotide fragments generated in step (c).

19. The method of claim 18, wherein the agent capable of cleaving a base portion of an unmethylated nucleotide comprises an enzyme.

20. The method of claim 19, wherein said unmethylated nucleotide is cytosine and the agent comprises cytosine deaminase in conjunction with uracil DNA glycosylase.

21. The method of claim 18, wherein the steps of the method are carried out simultaneously in the same reaction mixture.

22. The method of claim 18, wherein a polynucleotide captured in step (d) is captured on a microarray, a bead or by a probe in solution.

* * * * *